United States Patent
Wailes et al.

(10) Patent No.: US 11,434,221 B2
(45) Date of Patent: Sep. 6, 2022

(54) PYRAZINE-4-CARBAMATE OR -UREA DERIVATIVES AS HERBICIDES

(71) Applicant: Syngenta Participations AG, Basel (CH)

(72) Inventors: Jeffrey Steven Wailes, Bracknell (GB); Neil Brian Carter, Bracknell (GB); John Martin Clough, Bracknell (GB); John Williams, Bracknell (GB)

(73) Assignee: Syngenta Participations AG, Basel (CH)

( * ) Notice: Subject to any disclaimer, the term of this patent is extended or adjusted under 35 U.S.C. 154(b) by 161 days.

(21) Appl. No.: 16/649,615

(22) PCT Filed: Sep. 18, 2018

(86) PCT No.: PCT/EP2018/075231
§ 371 (c)(1),
(2) Date: Mar. 20, 2020

(87) PCT Pub. No.: WO2019/057725
PCT Pub. Date: Mar. 28, 2019

(65) Prior Publication Data
US 2020/0308137 A1    Oct. 1, 2020

(30) Foreign Application Priority Data
Sep. 22, 2017   (GB) .................... 1715414

(51) Int. Cl.
*A01N 43/60* (2006.01)
*C07D 401/04* (2006.01)
*C07D 403/04* (2006.01)

(52) U.S. Cl.
CPC ........... *C07D 401/04* (2013.01); *A01N 43/60* (2013.01); *C07D 403/04* (2013.01)

(58) Field of Classification Search
None
See application file for complete search history.

(56) References Cited

U.S. PATENT DOCUMENTS 6,710,048 B2 * 3/2004  Kuo .................... A61P 9/00
                                                     544/405

FOREIGN PATENT DOCUMENTS

| JP | 06192252 A    | 7/1994 |
| JP | 2015147757 A  | 8/2015 |
| WO | 2017162522 A1 | 9/2017 |

OTHER PUBLICATIONS

GB Search Report for GB Patent Application No. GB1715414.7 dated May 22, 2018.
International Search Report and Written Opinion for International Patent Application No. PCT/EP2018/075231 dated Nov. 22, 2018.
Martin Dolezal et al., Synthesis and Evaluation of Pyrazine Derivatives with Herbicidal Activity, Herbicides, Theory and Applications, Jan. 8, 2011, pp. 581-610.

* cited by examiner

*Primary Examiner* — Alton N Pryor
(74) *Attorney, Agent, or Firm* — BakerHostetler; Toni-Junell Herbert

(57) ABSTRACT

The present invention relates to herbicidally active pyridyl-/pyrimidyl-pyrazine derivatives, as well as to processes and intermediates used for the preparation of such derivatives. The invention further extends to herbicidal compositions comprising such derivatives, as well as to the use of such compounds and compositions in controlling undesirable plant growth: in particular the use in controlling weeds, in crops of useful plants.

15 Claims, No Drawings

PYRAZINE-4-CARBAMATE OR -UREA DERIVATIVES AS HERBICIDES

CROSS-REFERENCE TO RELATED APPLICATIONS

This application is a 371 National Stage application of International Application No. PCT/EP2018/075231 filed Sep. 18, 2018 which claims priority to GB 1715414.7, filed Sep. 22, 2017, filed in the United Kingdom, the entire contents of which applications are hereby incorporated by reference.

The present invention relates to herbicidally active pyridyl-/pyrimidyl-pyrazine derivatives, as well as to processes and intermediates used for the preparation of such derivatives. The invention further extends to herbicidal compositions comprising such derivatives, as well as to the use of such compounds and compositions in controlling undesirable plant growth: in particular the use in controlling weeds, in crops of useful plants.

Both WO2010/141275 and WO2010/071837 describe pyridyl-pyrazinecarboxylic acid derivatives for pharmaceutical use.

Certain pyridyl-pyrazine and pyrimidyl-pyrazine derivatives are known from JP2015-147757, where they are stated to have activity as insecticidal agents, and in particular acaricidal agents.

The present invention is based on the finding that pyridyl-pyrimidine, and pyrimidyl-pyrimidine, derivatives of Formula (I) as defined herein, exhibit surprisingly good herbicidal activity. Thus, according to the present invention there is provided a compound of Formula (I)

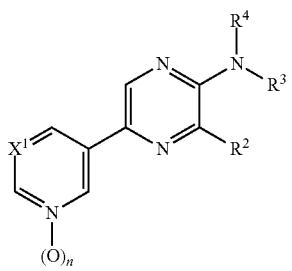

or a salt thereof, wherein, $X^1$ is N or $CR^1$;

$R^1$ is selected from the group consisting of hydrogen, halogen, cyano, $C_1$-$C_6$alkyl, $C_3$-$C_6$cycloalkyl, $C_2$-$C_6$alkenyl, $C_2$-$C_6$alkynyl, $C_1$-$C_6$alkoxy, —C(O)O$C_1$-$C_6$alkyl, —S(O)$_p$$C_1$-$C_6$alkyl, $NR^6R^7$, $C_1$-$C_6$haloalkoxy and $C_1$-$C_6$haloalkyl;

$R^2$ is selected from the group consisting of halogen, cyano, nitro, $C_1$-$C_6$alkyl, $C_1$-$C_6$haloalkyl, $C_2$-$C_6$alkenyl, $C_2$-$C_6$alkynyl, trimethylsilyl$C_2$-$C_6$alkynyl-, $C_3$-$C_6$cycloalkyl, $C_5$-$C_6$cycloalkenyl, —C(O)O$C_1$-$C_6$alkyl, —S(O)$_p$($C_1$-$C_6$alkyl), $C_1$-$C_6$alkoxy, $C_1$-$C_6$haloalkoxy, —(CR$^a$R$^b$)$_q$R$^{15}$, phenyl and benzyloxy;

$R^{15}$ is hydroxy, —C(O)OR$^c$, —OC(O)R$^c$, —$C_3$-$C_6$cycloalkyl, or an -aryl, -aryloxy, -heteroaryl, -heteroaryloxy or -heterocyclyl ring, wherein said ring is optionally substituted by 1 to 3 independent $R^8$;

$R^3$ is —C(O)X$^2$R$^{12}$;

$X^2$ is O or NR$^{10}$;

$R^4$ is selected from the group consisting of hydrogen, $C_1$-$C_6$alkyl, $C_1$-$C_6$alkoxy, $C_1$-$C_6$haloalkyl, $C_1$-$C_6$haloalkoxy, $C_3$-$C_6$cycloalkyl, $C_3$-$C_6$alkenyl, $C_3$-$C_6$alkynyl, —C(O)R$^9$—(CR$^a$R$^b$)$_q$R$^5$, —C(O)X$^3$R$^{13}$; or, when $X^2$ is O, $R^{12}$ is selected from the group consisting of $C_1$-$C_6$alkyl, $C_r$alkoxyC$_s$alkyl, $C_1$-$C_6$haloalkyl, $C_r$alkoxyC$_s$haloalkyl, $C_r$alkylthioC$_s$alkyl, $C_2$-$C_6$alkenyl, $C_2$-$C_6$alkynyl, and —(CR$^a$R$^b$)$_q$R$^{11}$, or $R^4$ and $R^{12}$ together with the heteroatoms to which they are joined form a 5-7 membered ring system optionally containing 1 additional heteroatom selected from S, O and N, wherein when said additional heteroatom is sulphur it is in the form S(O)$_p$.

when $X^2$ is $NR^{10}$, $R^{12}$ is selected from the group consisting of hydrogen, $C_1$-$C_6$alkyl, $C_1$-$C_6$alkoxy, $C_1$-$C_6$haloalkyl, $C_1$-$C_6$haloalkoxy, $C_r$alkylthioC$_s$alkyl, $C_2$-$C_6$alkenyl, $C_2$-$C_6$alkynyl, and —(CR$^a$R$^b$)$_q$R$^{11}$; or $R^{10}$ and $R^{12}$ together with the nitrogen atom to which they are both joined, can form a 5-, 6-, or 7-memberered ring, optionally containing 1 to 3 additional heteroatoms each independently selected from O, N or S, wherein when said ring contains a ring sulphur, said ring sulphur is in the form S(O)$_p$; or $R^4$ and $R^{10}$ together with the atoms to which they are joined form a 5-7 membered ring system optionally comprising from 1 or 2 additional heteroatoms independently selected from S, O and N and wherein when said ring system contains a ring sulphur, said ring sulphur is in the form S(O)$_p$; or, $R^{10}$ is independently selected from the group consisting of hydrogen, $C_1$-$C_6$alkyl, $C_3$-$C_6$ cycloalkyl;

when $R^4$ is —C(O)X$^3$R$^{13}$, $X^3$ is O or NR$^{14}$;

when $X^3$ is O, $R^{13}$ is selected from the group consisting of $C_1$-$C_6$alkyl, $C_r$alkoxyC$_s$alkyl, $C_1$-$C_6$haloalkyl, $C_r$alkoxyC$_s$haloalkyl, $C_r$alkylthioC$_s$alkyl, $C_2$-$C_6$alkenyl, $C_2$-$C_6$alkynyl, and —(CR$^a$R$^b$)$_q$R$^{11}$, or $R^3$ and $R^{13}$ together with the heteroatoms to which they are joined form a 5-7 membered ring system optionally containing 1 additional heteroatom selected from S, O and N, wherein when said additional heteroatom is sulphur it is in the form S(O)$_p$.

when $X^3$ is $NR^{14}$, $R^{13}$ is selected from the group consisting of hydrogen, $C_1$-$C_6$alkyl, $C_1$-$C_6$alkoxy, $C_1$-$C_6$haloalkyl, $C_1$-$C_6$haloalkoxy, $C_r$alkylthioC$_s$alkyl, $C_2$-$C_6$alkenyl, $C_2$-$C_6$alkynyl, and —(CR$^a$R$^b$)$_q$R$^{11}$; or $R^{14}$ and $R^{13}$ together with the nitrogen atom to which they are both joined, can form a 5-, 6-, or 7-memberered ring, optionally containing 1 or 2 additional heteroatoms each independently selected from O, N or S, wherein when said ring contains a ring sulphur, said ring sulphur is in the form S(O)$_p$;

$R^a$ is hydrogen or $C_1$-$C_2$ alkyl;

$R^b$ is hydrogen or $C_1$-$C_2$ alkyl;

$R^c$ is hydrogen or $C_1$-$C_4$alkyl;

$R^5$ is cyano, —C(O)O$C_1$-$C_6$alkyl, —$C_3$-$C_6$cycloalkyl, -aryl or -heteroaryl wherein said aryl and heteroaryl are optionally substituted by 1 to 3 independent $R^8$;

$R^6$ and $R^7$ are independently selected from the group consisting of hydrogen, $C_1$-$C_6$alkyl, and —C(O)O$C_1$-$C_4$alkyl;

each $R^8$ is independently selected from the group consisting of halogen, $C_1$-$C_6$alkyl and $C_1$-$C_6$alkoxy-, $C_1$-$C_6$ haloalkyl, $C_1$-$C_6$ haloalkoxy-, cyano and S(O)$_p$($C_1$-$C_6$alkyl);

$R^9$ is selected from the group consisting of hydrogen, $C_1$-$C_6$alkyl, $C_1$-$C_6$alkoxy, $C_1$-$C_6$haloalkyl, $C_1$-$C_6$haloalkoxy, $C_2$-$C_6$alkenyl, $C_2$-$C_6$alkynyl, and —(CR$^a$R$^b$)$_q$R$^{11}$;

$R^{11}$ is cyano, —$C_3$-$C_6$cycloalkyl, or an -aryl, -heteroaryl or -heterocyclyl ring, wherein said ring is optionally substituted by 1 to 3 independent $R^8$, and wherein when said ring contains a ring sulphur, said ring sulphur is in the form S(O)$_p$;

n is 0 or 1;

p is 0, 1, or 2;

q is 0, 1, 2, 3, 4, 5 or 6;

r is 1, 2, 3, 4, or 5, s is 1, 2, 3, 4, or 5, and the sum of r+s is less than or equal to 6.

Compounds of formula (I) may exist as different geometric isomers, or in different tautomeric forms. This invention covers the use of all such isomers and tautomers, and mixtures thereof in all proportions, as well as isotopic forms such as deuterated compounds.

It may be the case that compounds of formula (I) may contain one or more asymmetric centers and may thus give rise to optical isomers and diastereomers. While shown without respect to stereochemistry, the present invention includes the use of all such optical isomers and diastereomers as well as the racemic and resolved, enantiomerically pure R and S stereoisomers and other mixtures of the R and S stereoisomers and agrochemically acceptable salts thereof.

Each alkyl moiety either alone or as part of a larger group (such as alkoxy, alkylthio, alkoxycarbonyl, alkylcarbonyl, alkylaminocarbonyl, or dialkylaminocarbonyl, et al.) may be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups are generally $C_1$-$C_6$ alkyl groups (except where already defined more narrowly), but are preferably $C_1$-$C_4$ alkyl or $C_1$-$C_3$ alkyl groups, and, more preferably, are C1-C2 alkyl groups (such as methyl).

Alkenyl and alkynyl moieties can be in the form of straight or branched chains, and the alkenyl moieties, where appropriate, can be of either the (E)- or (Z)-configuration. Alkenyl and alkynyl moieties can contain one or more double and/or triple bonds in any combination; but preferably contain only one double bond (for alkenyl) or only one triple bond (for alkynyl).

The alkenyl or alkynyl moieties are typically $C_2$-$C_4$ alkenyl or $C_2$-$C_4$ alkynyl, more specifically ethenyl (vinyl), prop-2-enyl, prop-3-enyl (allyl), ethynyl, prop-3-ynyl (propargyl), or prop-1-ynyl. Preferably, the term cycloalkyl refers to cyclopropyl, cyclobutyl, cyclopentyl or cyclohexyl.

In the context of the present specification the term "aryl" preferably means phenyl. Heteroaryl groups and heteroaryl rings (either alone or as part of a larger group, such as heteroaryl-alkyl-) are ring systems containing at least one heteroatom and can be in mono- or bi-cyclic form. Typically "heteroaryl" is as used in the context of this invention includes furyl, thienyl, pyrrolyl, pyrazolyl, imidazolyl, triazolyl, oxazolyl, isoxazolyl, thiazolyl, isothiazolyl, oxadiazolyl, pyridyl, pyrimidinyl, pyridazinyl, pyrazinyl, and triazinyl rings, which may or may not be substituted as described herein.

The term "heterocyclyl" as used herein, encompasses ring systems containing at least one heteroatom and that are typically in monocyclic form. Preferably, heterocyclyl groups will contain up to two heteroatoms which will preferably be chosen from nitrogen, oxygen and sulfur. Where a heterocycle contains sulfur as a heteroatom it may be in oxidized form i.e. in the form —S(O)$_p$— where p is an integer of 0, 1 or 2 as defined herein. Such heterocyclyl groups are preferably 3- to 8-membered, and more preferably 3- to 6-membered rings. Examples of heterocyclic groups include oxetanyl, thietanyl, and azetidinyl groups. Such heterocyclyl rings may or may not be substituted as described herein.

Halogen (or halo) encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. It should also be appreciated that two alkoxy substituents may be present on the same carbon atom.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_1$-$C_6$ alkyl-S-(alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$ alkyl-S(O)-(alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$ alkyl-S(O)$_2$-(alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Compounds of formula (I) may form, and/or be used as, agronomically acceptable salts with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used in salt formation, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

Compounds of formula (I) may also form (and/or be used as) agronomically acceptable salts with various organic and/or inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids, when the compound of formula (I) contains a basic moiety.

Where appropriate compounds of formula (I) may also be in the form of/used as an N-oxide.

Compounds of formula (I) may also be in the form of/used as hydrates which may be formed during the salt formation.

Preferred values of $X^1$, $X^2$, $X^3$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^a$, $R^b$, $R^c$ n, p, q, r and s are as set out below, and a compound of formula (I) according to the invention may comprise any combination of said values. The skilled person will appreciate that values for any specified set of embodiments may combined with values for any other set of embodiments where such combinations are not mutually exclusive.

The skilled man will also appreciate that the values or r and s in the definitions $C_r$alkoxy$C_s$alkyl and $C_r$alkoxy$C_s$haloalkyl are such that the length of the carbon chain within the substituent does not exceed 6. Preferred values of r are 1, 2, or 3. Preferred values for s are 1, 2, or 3. In various embodiments r is 1, s is 1; or, r is 1, s is 2; or r is 1, s is 3; or r is 2, s is 1; r is 2, s is 2; or r is 2, s is 3; or r is 3, s is 1; or r is 3, s is 2, r is 3, s is 3. Particularly preferred substituents thus include methoxymethyl, and ethoxymethyl.

In one particular embodiment of the present invention, $X^1$ is N.

In another embodiment of the present invention, $X^1$ is $CR^1$ and $R^1$ is preferably selected from the group consisting of cyano, halogen, $C_1$-$C_6$alkoxy, $C_1$-$C_6$haloalkoxy, $C_1$-$C_6$haloalkyl, and —$S(O)_pC_1$-$C_6$alkyl. More preferably $R^1$ is selected from the group consisting of cyano, fluoro, chloro, methoxy, difluoromethoxy, trifluoromethyl and thiomethyl. More preferably still, $R^1$ is selected from the group consisting of cyano, fluoro, chloro, methoxy, trifluoromethyl and thiomethyl. Even more preferably still, $R^1$ is cyano, fluoro, or thiomethyl.

Preferably $R^2$ is selected from the group consisting of halogen, cyano, $C_1$-$C_4$alkyl, $C_3$-$C_6$cycloalkyl, $C_1$-$C_4$alkoxy, $C_1$-$C_4$haloalkyl, $C_1$-$C_4$thioalkyl, $C_2$-$C_4$alkenyl, $C_5$-$C_6$cycloalkenyl, $C_2$-$C_4$alkynyl, trimethylsilyl$C_2$-$C_4$alkynyl-, —$C(O)OC_1$-$C_4$alkyl, —$(CR^aR^b)_qR^{15}$, phenyl, and benzyloxy. More preferably $R^2$ is halogen, cyano, $C_1$-$C_3$alkyl, cylcopropyl, $C_1$-$C_2$alkoxy, $C_1$-$C_2$haloalkyl, $C_1$-$C_2$thioalkyl, $C_2$-$C_4$alkenyl, $C_5$-$C_6$cycloalkenyl, acetylene, trimethylsilylacetylene-, —$C(O)OC_1$-$C_4$alkyl, —$CH_2OH$, and -benzyloxy.

Where $X^2$ is O (i.e. where $R^3$ is —$C(O)OR^{12}$), $R^{12}$ is preferably selected from the group consisting of hydrogen, $C_1$-$C_6$alkyl, $C_r$alkoxy$C_s$alkyl, $C_1$-$C_6$haloalkyl, $C_r$alkoxy$C_s$haloalkyl, $C_r$alkylthio$C_s$alkyl, $C_2$-$C_6$alkenyl, $C_2$-$C_6$alkynyl, and —$(CR^aR^b)_qR^{11}$. In such embodiments, $R^{12}$ is preferably $C_1$-$C_4$alkyl, $C_1$-$C_4$ haloalkyl, $C_1$-$C_3$alkoxy$C_1$-$C_3$alkyl, $C_1$-$C_3$alkylthio$C_1$-$C_3$alkyl, or $CR^aR^b_qR^{11}$, wherein q is 0, 1 or 2, $R^a$ and $R^b$ are each hydrogen, and $R^{11}$ is cyano, $C_3$-$C_6$cycloalkyl, a 5- or 6-membered heterocycle containing 1 or 2 heteroatoms independently selected from O and S wherein said S is in the form $S(O)_p$, or phenyl optionally substituted by 1-3 $R^8$.

In one set of embodiments, $R^3$ is —$C(O)OC_1$-$C_6$alkyl, and preferably selected from the group consisting of —$C(O)$O-methyl, —$C(O)$O-ethyl, —$C(O)$O-n-propyl, —$C(O)$O-iso-propyl, —$C(O)$O-iso-butyl, —$C(O)$O-sec-butyl, and —$C(O)$O-tert-butyl. It is particularly preferred in such embodiments that $R^3$ is —$C(O)$O-tert-butyl.

Where $X^2$ is $NR^{10}$ (i.e. where $R^3$ is —$C(O)NR^{10}R^{12}$) it is preferred that $R^{10}$ is hydrogen or $C_1$-$C_6$alkyl (in particular methyl), or that it forms a 5-7 membered (preferably 5- or 6-membered) ring system optionally containing from 1 to 3 additional heteroatoms independently selected from S in the form of $S(O)_p$, O and N, in conjunction either with $R^4$ and the atoms to which $R^{10}$ and $R^4$ are joined, or in conjunction with $R^{12}$ and the nitrogen atom to which $R^{10}$ and $R^{12}$ are joined. In embodiments where $R^4$ and $R^{10}$ are joined, the skilled man will appreciate that the ring system may appear as a substituted ring system bearing a substituent on the nitrogen atom of group $NR^{10}$, by virtue of substituent $R^{12}$. In these embodiments it is preferred that $R^{12}$ is hydrogen, or $C_1$-$C_6$ alkyl; preferably hydrogen or $C_1$-$C_3$ alkyl; and more preferably hydrogen or methyl.

In embodiments where $R^{10}$ and $R^{12}$ together with the nitrogen atom to which they are joined form a ring system, it is preferred that said ring system is 5- or 6-membered. Where the ring system is 5-membered, it will preferably contain 0 or 1 additional heteroatom independently selected from O, N, or S in the form of $S(O)_p$. More preferably the 1 additional heteroatom will be S in the form of $S(O)_p$. Where the ring system is 6-membered, it will preferably contain 0 or 1 additional heteroatom independently selected from O, N, or S in the form of $S(O)_p$. More preferably the 1 additional heteroatom will be O or N, most preferably N. In one set of embodiments $R^{10}$ and $R^{12}$ together with the N-atom to which they are joined form a morpholine ring.

Where $R^{10}$ does not form a ring with either $R^4$ or $R^{12}$, and is hydrogen or $C_1$-$C_6$alkyl (preferably hydrogen or methyl), it is preferred that $R^{12}$ is $C_1$-$C_4$alkyl, $C_1$-$C_3$alkoxy, $(CH_2)_3$ $SCH_3$, $C_1$-$C_3$haloalkyl, $C_3$-$C_6$alkynyl, or $(CR^aR^b)_qR^{11}$. In such embodiments where $R^{12}$ is $(CR^aR^b)_qR^{11}$, it is particularly preferred that q is 0 or 1. It is further preferred that $R^{11}$ in such embodiments is an optionally substituted ring system selected from the group consisting of $C_3$-$C_6$cycloalkyl, isoxazolyl, phenyl, pyridyl, pyrimidinyl, tetrahydropyranyl and morpholinyl, which, when substituted, is substituted by 1-3 independent $R^8$.

Preferably, where $R^4$ does not form a ring with either $R^{10}$ or $R^{12}$, $R^4$ is selected from the group consisting of hydrogen, methyl, ethyl, allyl, but-2-yn-1-yl, $C(O)R^9$ where $R^9$ is preferably $C_1$-$C_6$alkoxy, and —$(CH_2)_qR^5$ wherein q is 1 and $R^5$ is selected from the group consisting of c-propyl, —$CO_2$methyl, and phenyl optionally substituted by 1-2 groups $R^8$, wherein each $R^8$ is independently $C_1$-$C_3$alkyl or halogen (more preferably in such embodiments $R^8$ is methyl or fluoro). More preferably $R^4$ is selected from the group consisting of hydrogen, methyl, allyl, propoxycarbonyl, and butoxycarbonyl. More preferably still $R^4$ is selected from the group consisting of hydrogen, methyl and butoxycarbonyl.

In an alternative embodiment of the present invention, $R^4$ and $R^{10}$ together with the atoms to which they are joined form a 5-7 membered ring system optionally containing from 1 to 3 heteroatoms independently selected from S, O and N, as described supra.

In yet a further alternative embodiment, $R^4$ and $R^{12}$ together with the atoms to which they are joined form a 5-7 membered ring system optionally containing 1 or 2 additional heteroatoms independently selected from S, O and N. Where an additional heteroatom is S, it will be in the form of $S(O)_p$. Preferably said ring system is 6-membered.

In one embodiment $R^6$ and $R^7$ are both hydrogen. In another embodiment $R^6$ is hydrogen and $R^7$ is $C_1$-$C_6$alkyl (e.g., methyl or ethyl). In another embodiment, $R^6$ and $R^7$ are both $C_1$-$C_6$alkyl. In yet a further embodiment $R^6$ is hydrogen and $R^7$ is —$C(O)OC_4$alkyl (in particular —$C(O)$O-tert-butyl).

Preferably $R^9$ is $C_1$-$C_6$alkyl, preferably ethyl, propyl (in particular iso-propyl) or butyl (in particular tert-butyl).

Preferably $R^{11}$ is selected from the group consisting of $C_3$-$C_6$cycloalkyl, phenyl optionally substituted by 1-3 $R^8$, a 5- or 6-membered unsubstituted heteroaryl or 5- or 6-membered unsubstituted heterocyclyl ring, and a 5- or 6-membered heteroaryl or 5- or 6-membered heterocyclyl ring, each substituted by 1-3 $R^8$. When said phenyl, heterocyclyl or heteroaryl ring is substituted, it is preferably substituted by 1 or 2 $R^8$.

Preferably each $R^8$ is independently selected from halogen, $C_1$-$C_3$-alkyl or $C_1$-$C_3$haloalkyl. More preferably each $R^8$ is independently selected from methyl, ethyl, chloro or fluoro, more preferably still methyl or chloro.

Table 1 below provides 33 specific examples of herbicidal compounds of Formula (I) for use according to the invention.

TABLE 1

Specific examples of compounds of Formula (I-H) (which are compounds of formula (I) wherein n is 0 and $X^1$, $R^2$, $R^3$, and $R^4$ are given in the table) for use in the invention.

(I-H)

| Compound ID | $X^1$ | $R^2$ | $R^3$ | $R^4$ |
|---|---|---|---|---|
| H1 | N | $CF_3$ | $CO_2tBu$ | $CO_2tBu$ |
| H2 | C—F | $CH_3$ | $CO_2tBu$ | $CO_2tBu$ |
| H3 | N | $CF_3$ | $CO_2tBu$ | H |
| H4 | C—F | $CF_3$ | $CO_2tBu$ | H |
| H5 | C—F | $CF_3$ | $CO_2tBu$ | $CO_2tBu$ |
| H6 | C—F | $OCH_3$ | $CO_2tBu$ | $CO_2tBu$ |
| H7 | C—F | $OCH_3$ | $CO_2tBu$ | H |
| H8 | C—F | $OCH_2Ph$ | $CO_2tBu$ | $CO_2tBu$ |
| H9 | C—F | CN | $CO_2tBu$ | $CO_2tBu$ |
| H10 | C—F | CN | $CO_2tBu$ | H |
| H11 | C—F | isopropenyl | $CO_2tBu$ | $CO_2tBu$ |
| H12 | C—F | 1-methylcyclopropyl | $CO_2tBu$ | $CO_2tBu$ |
| H13 | C—F | isopropyl | $CO_2tBu$ | $CO_2tBu$ |
| H14 | C—F | $CH=C(CH_3)_2$ | $CO_2tBu$ | $CO_2tBu$ |
| H15 | C—F | cyclohex-1-enyl | $CO_2tBu$ | $CO_2tBu$ |
| H16 | C—F | Br | $CO_2tBu$ | $CO_2tBu$ |
| H17 | C—F | $CH_3$ | $CO_2tBu$ | H |
| H18 | C—F | $CH_2OCO_2tBu$ | $CO_2tBu$ | $CO_2tBu$ |
| H19 | C—F | $CH_3$ | $CO_2tBu$ | $CH_3$ |
| H20 | C—F | $CH=CH_2$ | $CO_2tBu$ | $CO_2tBu$ |
| H21 | C—F | $CH_2CH_3$ | $CO_2tBu$ | $CO_2tBu$ |
| H22 | C—F | $CH_2OH$ | $CO_2tBu$ | H |
| H23 | N | $CH_3$ | $CO_2tBu$ | H |
| H24 | C—F | $SCH_3$ | $CO_2tBu$ | H |
| H25 | C—$SCH_3$ | $SCH_3$ | $CO_2tBu$ | H |
| H26 | CF | $CO_2CH_3$ | $CO_2tBu$ | $CO_2tBu$ |
| H27 | C—F | $CF_2H$ | $CO_2tBu$ | $CO_2tBu$ |
| H28 | C—F | $CF_2H$ | $CO_2tBu$ | H |
| H29 | C—F | 1,1-dimethylprop-2-ynyl | $CO_2tBu$ | $CO_2tBu$ |

TABLE 1-continued

Specific examples of compounds of Formula (I-H) (which are compounds of formula (I) wherein n is 0 and $X^1$, $R^2$, $R^3$, and $R^4$ are given in the table) for use in the invention.

(I-H)

| Compound ID | $X^1$ | $R^2$ | $R^3$ | $R^4$ |
|---|---|---|---|---|
| H30 | N | $CF_2H$ | $CO_2tBu$ | H |
| H31 | N | $CF_2H$ | $CO_2tBu$ | $CO_2tBu$ |
| H32 | C—F | —C≡C—Si(CH₃)₃ | $CO_2tBu$ | $CO_2tBu$ |
| H33 | C—F | —C≡C—Si(CH₃)₃ | $CO_2tBu$ | H |

Compounds of Formula (I) may be prepared according to the following schemes, in which the substituents of $X^1$, $X^2$, $X^3$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^a$, $R^b$, $R^c$ n, p, q r and s have (unless otherwise stated explicitly) the definitions described hereinbefore, using techniques known to the person skilled in the art of organic chemistry. General methods for the production of compounds of formula (I) are described below. The starting materials used for the preparation of the compounds of the invention may be purchased from the usual commercial suppliers or may be prepared by known methods. The starting materials as well as the intermediates may be purified before use in the next step by state of the art methodologies such as chromatography, crystallization, distillation and filtration.

Typical abbreviations used throughout are as follows:
app=apparent
br.=broad
$^t$Bu=tert-butyl
t-BuOH=tert-butanol
d=doublet
dd=double doublet
DCM=dichloromethane
DMF=N, N-dimethylformamide
DMSO=dimethylsulfoxide
DPPA=diphenylphosphoryl azide
$Et_3N$=triethylamine
$Et_2O$=diethyl ether
EtOAc=ethyl acetate
EtOH=ethanol
HPLC=High Performance Liquid Chromatography
m=multiplet
Me=methyl
MeOH=methanol
Ph=phenyl
q=quartet
RT or rt=room temperature
s=singlet
t=triplet
TFA=trifluoroacetic acid
THF=tetrahydrofuran
TMS=tetramethylsilane
tr=retention time Processes for preparation of compounds, e.g. a compound of formula (I) (which optionally can be an agrochemically acceptable salt thereof), are now described, and form further aspects of the present invention. A summary of approaches will be described first, and this will be followed by more detailed descriptions of some of the preferred approaches and transformations.

It should be understood by those skilled in the art that the various transformations by which the compounds of the invention can be prepared, may be carried out in a variety of orders. For example, the bond between the two heterocycles can be made by a cross-coupling reaction, after which the groups $NR^3R^4$ and $R^2$ may be introduced or modified, or the cross-coupling reaction may be the final step in a sequence of reactions leading to the compounds of the invention.

The pyrazines of Formula (I) can be prepared by the following eight key steps:

(A) Linking the two heteroaromatic rings by cross-coupling. In one preferred approach, cross-coupling is a Suzuki reaction in which a 3-pyridyl- or 5-pyrimidinyl-boronic acid reacts with a halo-pyrazine, but either heterocycle can carry the required metallic (or quasi-metallic) functional group, and either can carry the complementary halogen or other leaving group, e.g. $OSO_2CF_3$.

(B) Regioselective introduction of functional groups to the pyrazine ring, e.g. bromination at the 5-position of a 2-amino-pyrazine, after which the new functional groups may be further modified.

(C) Formation of the group $NR^3R^4$ by modification of a group $NH^2$, $NHR^3$ or $NHR^4$, for example by alkoxyacylation (to form a carbamate), acylation, alkylation (either directly or by formation and then reduction of an imine, i.e. reductive amination), or by Curtius rearrangement of a carboxyl group, or by Hofmann rearrangement of a primary carboxamide. In turn, a group NH2 may be prepared, for example, by reduction of a nitro or azido group, or by hydrolysis of the product of a Curtius or Hofmann rearrangement.

(D) Introduction of the group $NR^3R^4$ (or a group $NHR^3$ or $NHR^4$) by displacement of a halogen or an alternative leaving group, e.g. $OSO_2CF_3$.

(E) Direct introduction of the group $R^2$, or introduction of the group $R^2$ by displacement of a leaving group at the same position on the pyrazine ring, or construction of the group $R^2$ from another group at the same position on the pyrazine ring.

(F) N-Oxidation of the pyridine or pyrimidine ring.

(G) De novo synthesis of the pyrazine ring.

A more detailed description of some of the preferred transformations and approaches will now be given, all shown for compounds of the invention and intermediates in which n=0.

Compounds of Formula Ia are compounds of the invention of Formula (I) in which $X^2$=O, and compounds of Formula Ib are compounds of the invention of Formula (I) in which $X^2$=NR10.

Formula Ia

Formula Ib

A compound of Formula Ia can be prepared from a compound of Formula 1 using, for example, an alkoxycarbonyl alkyl carbonate of formula $(R^{12}O.CO)_2O$, or a chloroformate of formula $R^{12}O.COCl$, optionally in the presence of a suitable base, and in a suitable solvent, as shown in Scheme 1. If $R^4$=H in the compound of Formula 1, alkoxyacylation can take place either once or twice, leading to a compound of the invention of Formula Ia in which $R^4$=H or in which $R^4$=$CO_2R^{12}$. Reaction conditions, including ratios of reactants, can be chosen to favour one or other of these two products. For examples of reactions of these types, see S Régnier et al., J. Org. Chem., 2016, 81, 10348; International Patent Publication Nos. WO 2009/037247, WO 2008/153752; and K Tsuzuki and M Tada, J Het. Chem., 1986, 23, 1299.

Scheme 1

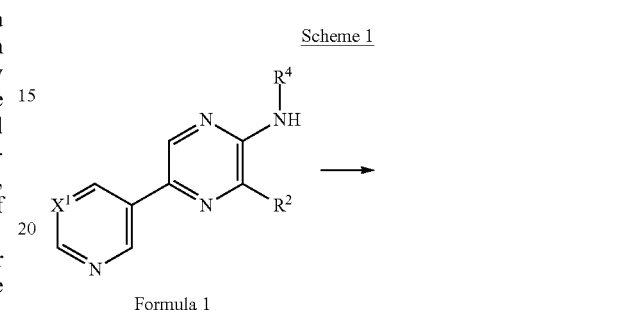

Formula 1

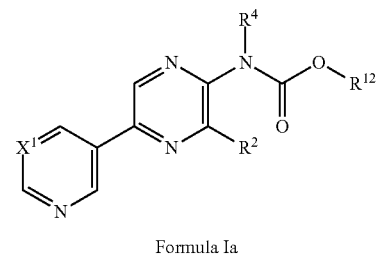

Formula Ia

Alternatively, a compound of Formula Ia can be prepared by treatment of an isocyanate of Formula 2 with an alcohol of formula $R^{12}OH$, in a suitable solvent (see, for example, F Fernandez et al., Bioorg. and Med. Chem., 2009, 17, 3618). Isocyanates of Formula 2 can be prepared by treatment of the corresponding amino-pyrazines with phosgene or an equivalent reagent such as triphosgene (see, for example, J S Nowick et al., J. Org. Chem., 1992, 57, 7364 and P Majer and R S Randad, J. Org. Chem., 1994, 59, 1937). Alternatively, isocyanates of Formula 2 can be prepared from the corresponding pyrazine-2-carboxylic acids by a Curtius rearrangement or one of the related rearrangements, as described in scheme 2 below.

Scheme 2

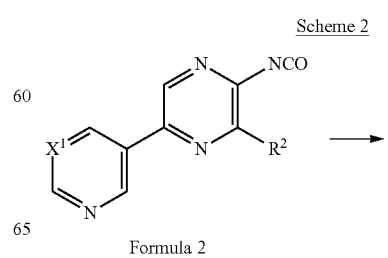

Formula 2

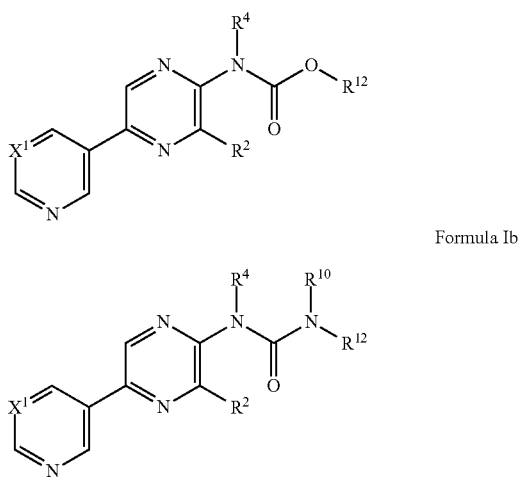

-continued

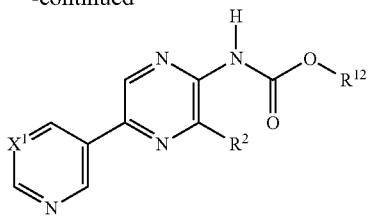

Formula Ia

A compound of Formula Ia in which $R^4$ is not hydrogen can be prepared from a compound of Formula Ia in which $R^4$=H, as shown in Scheme 3. If $R^4$=CO$_2$R$^{12}$ in the product of this reaction, the conversion can be carried out in the same way as described above (Scheme 1), and similar reactions will lead to compounds of Formula Ia in which $R^4$=acyl. If $R^4$=alkyl, alkoxyalkyl, haloalkyl, haloalkoxyalkyl, cycloalkyl, allyl or propargyl in the product, the reaction can be carried out using a suitable reagent of formula $R^4$-LG, in which LG is a leaving group such as a halogen or OSO$_2$CH$_3$, optionally in the presence of a base, and in a suitable solvent (see, for example, M Chioua et al., Eur. J. Org. Chem., 2013, 35). Compounds of formula $R^4$-LG are commercially available or can be prepared by methods described in the literature.

Scheme 3

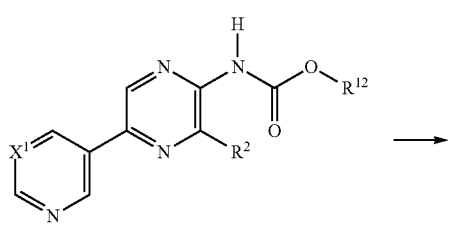

Formula Ia
$R^4$ = H

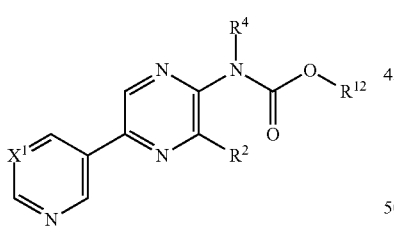

Formula Ia
$R^4$ is not H

A compound of Formula Ib in which $R^{10}$ and $R^{12}$ are not hydrogen can be prepared from a compound of Formula 1 by treatment with a carbamoyl chloride of formula $R^{10}R^{12}$N.CO.Cl, in a suitable solvent, and usually in the presence of a base, as shown in Scheme 4 (see, for example, Boehringer Ingelheim International GMBH, WO 2008/113760). Carbamoyl chlorides of formula $R^{10}R^{12}$N.CO.Cl are commercially available or can be prepared by methods described in the literature.

A compound of Formula Ib in which $R^{10}$=H can be prepared by treatment of a compound of Formula 1 with an isocyanate of formula $R^{12}$NCO, in a suitable solvent and optionally in the presence of a base, as shown in Scheme 4 (see, for example, G Heinisch et al., J. Het. Chem., 1995, 32, 13). Isocyanates of formula $R^{12}$NCO can be prepared, for example, from the corresponding primary amines of formula $R^{12}$NH2, or by Curtius rearrangement of carboxylic acids of formula $R^{12}$CO2H, using methods described in the literature.

Scheme 4

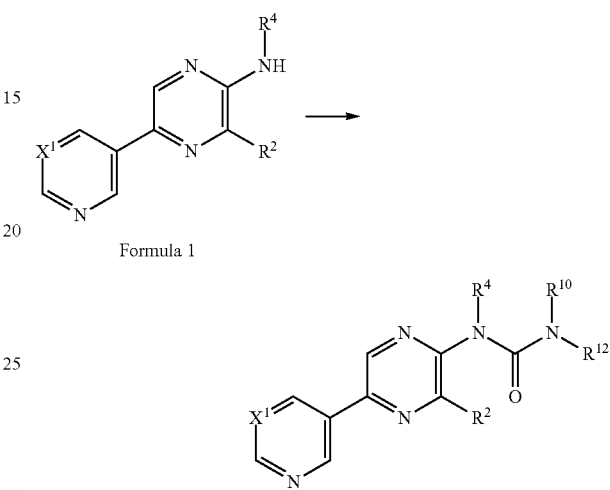

Formula 1

Formula Ib

A compound of Formula Ib can be made from a compound of Formula 3 in which U is a leaving group such as imidazol-1-yl or aryloxy by treatment with an amine of formula $R^{10}R^{12}$NH, in a suitable solvent, and optionally in the presence of a suitable base, as shown in Scheme 5.

Scheme 5

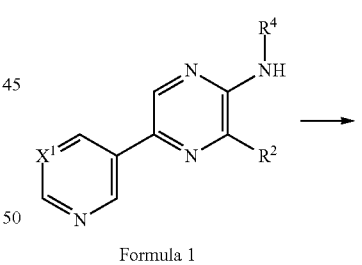

Formula 1

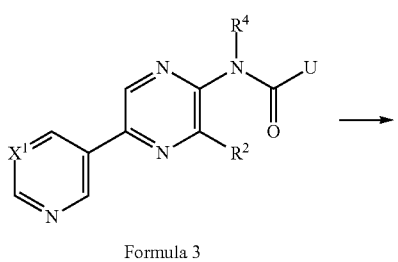

Formula 3

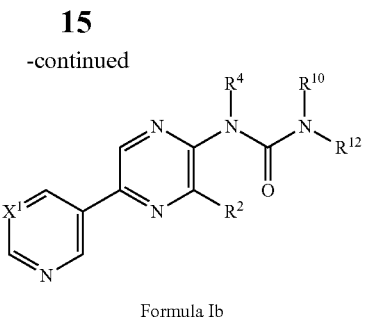

Formula Ib

In turn, a compound of Formula 3 can be made from a compound of Formula 1 by treatment, for example, with 1,1′-carbonyldiimidazole (U=imidazol-1-yl) or an aryl chloroformate (U=aryloxy), in a suitable solvent in each case and, for the aryl chloroformate, usually in the presence of a base, as shown above in Scheme 5.

For examples of reactions of this kind using 1,1′-carbonyldiimidazole, see International Patent Publication No. WO 2005/066145. For examples of reactions of this kind using phenyl chloroformate, see International Patent Publication No. WO 2008/153752.

A compound of Formula Ib in which $R^4$=H can be made from an isocyanate of Formula 2 by treatment with an amine of formula $R^{10}R^{12}NH$, in a suitable solvent. See, for example, R Aslanian et al., Bioorg. Med. Chem. Letts., 2002, 12, 937.

Scheme 6

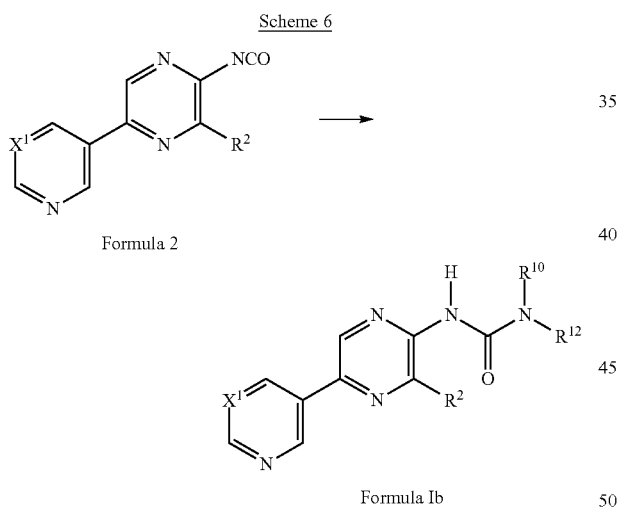

Formula 2

Formula Ib

A compound of Formula Ib in which $R^4$ is not hydrogen can be prepared from a compound of Formula Ib in which $R^4$=H, as shown in Scheme 7. If $R^4$=$CO_2R^{12}$ in the product, the conversion can be carried out in the same way as described above (Scheme 1), and similar reactions will lead to compounds of Formula Ia in which $R^4$=acyl. If $R^4$=alkyl, alkoxyalkyl, haloalkyl, haloalkoxyalkyl, cycloalkyl, allyl or propargyl in the product, the reaction can be carried out using a suitable reagent of formula $R^4$-LG, in which LG is a leaving group such as a halogen or $OSO_2CH3$, optionally in the presence of a base, and in a suitable solvent (see, for example, Abbott GMBH & CO. K.G., WO 2008/046919). Compounds of formula $R^4$-LG are commercially available or can be prepared by methods described in the literature.

Scheme 7

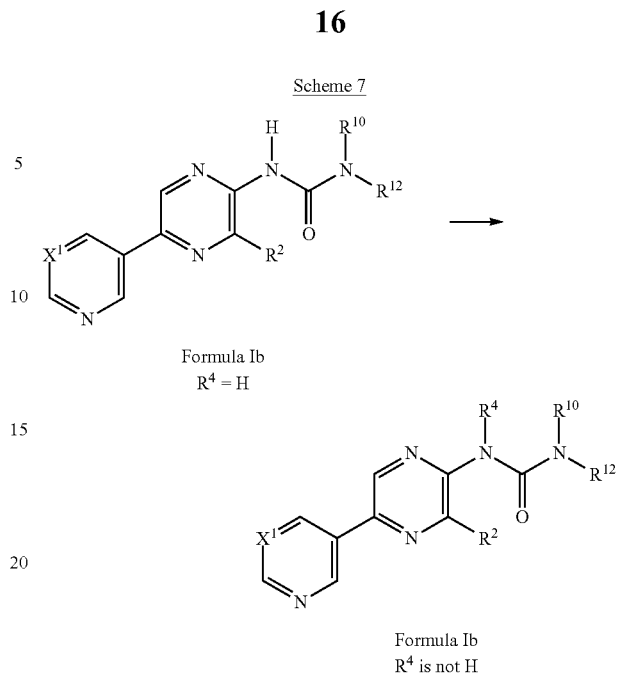

Formula Ib
$R^4$ = H

Formula Ib
$R^4$ is not H

A compound of Formula 1 in which $R^4$ is alkyl, alkoxyalkyl, haloalkyl, haloalkoxyalkyl, cycloalkyl, allyl or propargyl can be prepared from a compound of Formula 4 by treatment with a reagent $R^4$-LG, in which LG is a leaving group such as a halogen or $OSO_2CH3$, optionally in the presence of a base, and in a suitable solvent, as shown in Scheme 8 (see, for example, P Jeanjot et al., Synthesis, 2003, 513). Compounds of formula $R^4$-LG are commercially available or can be prepared by methods described in the literature.

Scheme 8

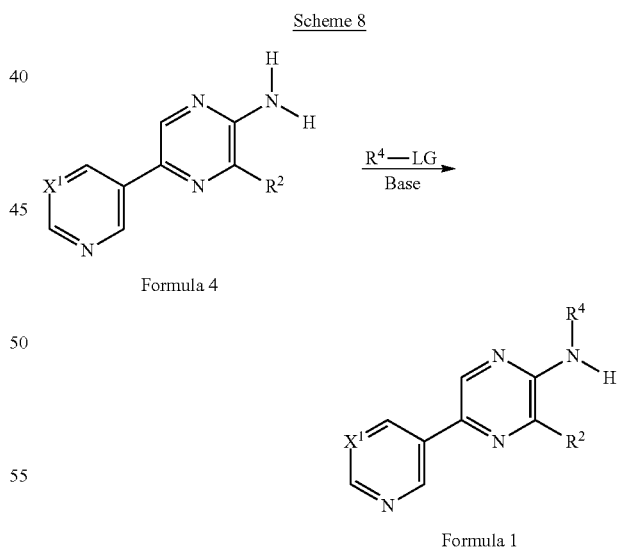

Formula 4

Formula 1

Amino-pyrazines can also be mono-methylated on the amino-group using methanol, sodium hydroxide and an iridium catalyst (see F Li et al., RSC Advances, 2012, 2, 8645). Related N-alkylations using other alcohols have also been reported (see, for example, S Li et al., Green Chem., 2015, 17, 3260).

In an alternative approach, a compound of Formula 1 in which $R^4$ is not hydrogen can be prepared from a compound of Formula 4 by reaction with an aldehyde $R^W$—CHO, in which $R^W$—$CH_2$=$R^4$, in the presence of a reducing agent, and in a suitable solvent, as shown in Scheme 9 (for examples, see P Jeanjot et al., Synthesis, 2003, 513). Ketones can also be used instead of the aldehyde $R^W$—CHO, and lead to branched substituents on the amino group (see, for example, International Patent Publication No. WO 2011/073149). Aldehydes of formula $R^W$—CHO and the corresponding ketones are commercially available or can be prepared by methods described in the literature.

a suitable halogen, such as Cl, Br or I, or another suitable leaving group, such as $OSO_2CF_3$, by reaction with an amine of formula $R^4NH_2$, optionally in the presence of a suitable catalyst and/or a suitable ligand and/or a suitable base, and in a suitable solvent, as shown in Scheme 10. For examples of reactions of this kind, see A J Henderson et al., Bioorg. and Med. Chem. Letts., 2010, 20, 1137, and P J J Colbon et al., J Het. Chem., 2008, 45, 1451. Amines of formula $R^4NH2$ are commercially available or can be prepared by methods described in the literature.

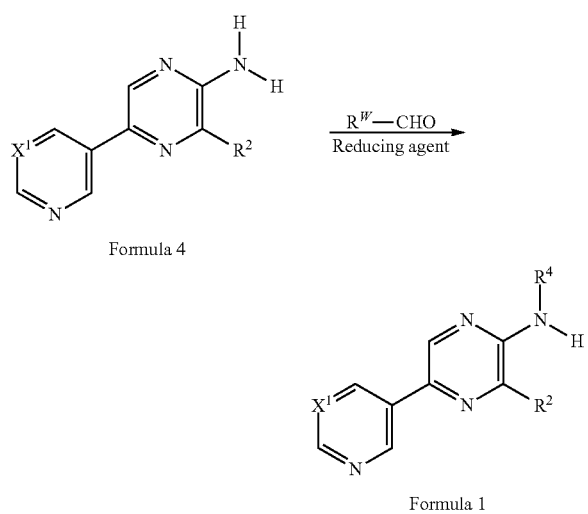

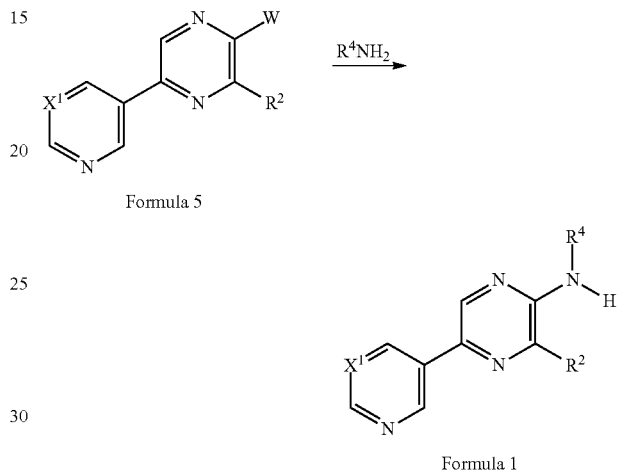

Amino-pyrazines can also be mono-alkylated (or mono-benzylated, etc.) by acylation at the amino-group and then reduction of the resulting amide using, for example, lithium aluminium hydride, in a suitable solvent (for examples, see P Jeanjot et al., Synthesis, 2003, 513).

In an alternative approach, a compound of Formula 1 may be prepared from a compound of Formula 5, in which W is A compound of the invention of Formula Ia may also be prepared by reaction of a pyrazine of Formula 5, in which W is a suitable halogen, such as Cl, Br or I, or another suitable leaving group, such as $OSO_2CF_3$, with a carbamate of formula $R^{12}O.C(O).NHR^4$, optionally in the presence of a suitable catalyst and/or a suitable ligand and/or a suitable base, and in a suitable solvent, as shown in Scheme 11.

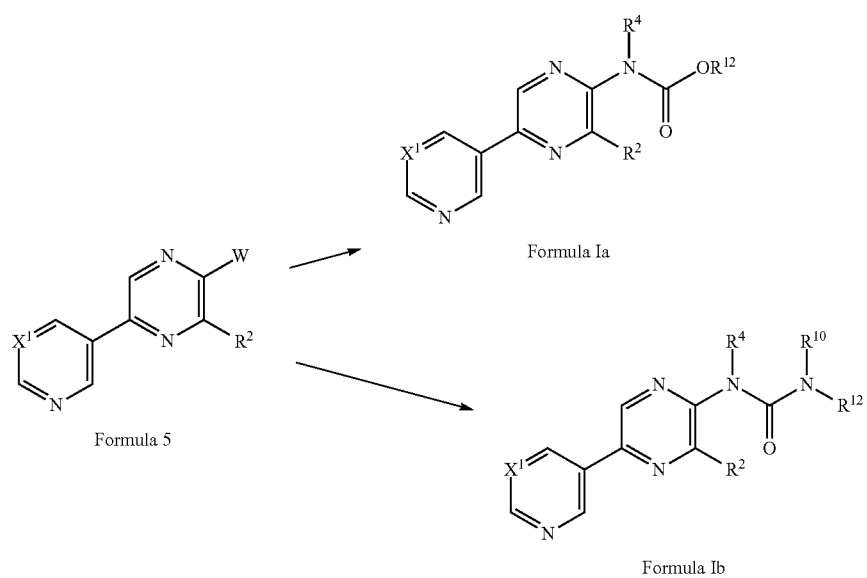

For examples of reactions of this kind, with and without palladium catalysis, see International Patent Publication No. WO 03/000666 and D Falcone et al., Tet. Letts., 2014, 55, 2646. Carbamates of formula $R^{12}O.C(O).NHR^4$ are commercially available or may be prepared by methods described in the literature.

In a similar way, a compound of the invention of Formula Ib may be prepared by reaction of a pyrazine of Formula 5 with a urea of formula $R^{10}R^{12}N.C(O).NHR^4$, optionally in the presence of a suitable catalyst and/or a suitable ligand and/or a suitable base, and in a suitable solvent, as shown above in Scheme 11. For examples of related reactions, see J B Ernst et al., Org. Letts., 2014, 16, 3844. Ureas of formula $R^{10}R^{12}N.C(O).NHR^4$ are commercially available or may be prepared by methods described in the literature.

A compound of Formula 4 can be prepared by reduction of the corresponding nitro-compound, optionally in the presence of a catalyst, and in a suitable solvent, as shown in Scheme 12 (see, for example, International Patent Publication No. WO 2013/078254).

Scheme 12

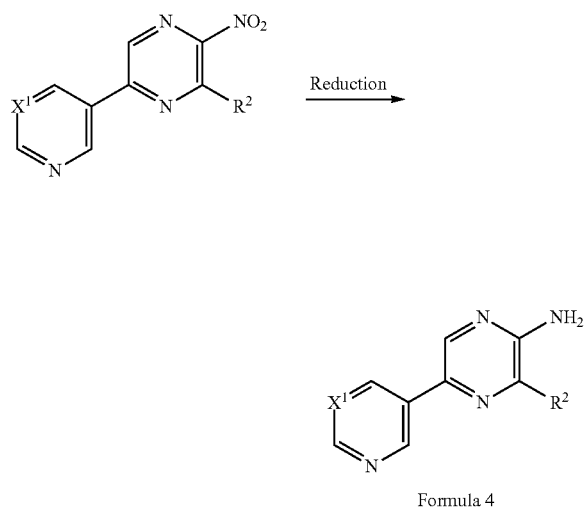

Formula 4

Similarly, a compound of Formula 4 can be prepared by reduction of the corresponding azide, optionally in the presence of a catalyst and in a suitable solvent (see, for example, N Sato et al., Synthesis, 1994, 931).

In an alternative approach, a compound of the invention of Formula Ia in which $R^4$=H can be prepared by a Curtius rearrangement of the corresponding carboxylic acid, in a suitable solvent, as shown in Scheme 13.

Scheme 13

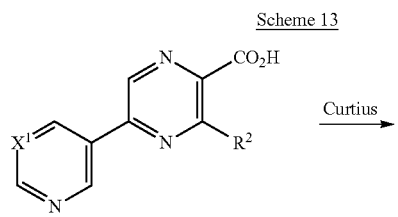

Curtius

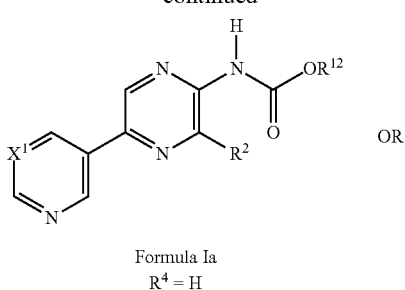

Formula Ia
$R^4$ = H

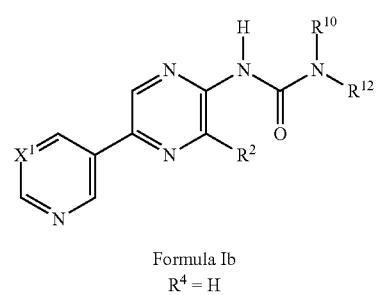

Formula Ib
$R^4$ = H

The first-formed product of the rearrangement is an isocyanate, but treatment with an alcohol of formula $R^{12}OH$, usually in the same reaction vessel, leads to a compound of the invention of Formula Ia in which $R^4$=H. Alternatively, the intermediate isocyanate can be hydrolysed to give the amino-pyrazine of Formula 4. For examples of Curtius reactions of this kind, see S Sunami and M Ohkubo, Tetrahedron, 2009, 65, 638. The starting carboxylic acids shown in Scheme 13 can be prepared, for example, by hydrolysis of the corresponding methyl or ethyl esters.

Compounds of the invention of Formula Ib in which $R^4$=H can also be prepared by a Curtius rearrangement, the first-formed isocyanate being treated with an amine of formula $R^{10}R^{12}NH$. For examples of Curtius reactions of this kind, see Millenium Pharmaceuticals, Inc., WO 03/101444.

The same transformations can also be carried out using the Schmidt reaction or the Lossen rearrangement.

In a related approach, a compound of the invention of Formula Ia in which $R^4$=H can be prepared by a Hofmann rearrangement of the corresponding primary carboxamide, in a suitable solvent, as shown in Scheme 14 (see, for example, G Madhusudhan et al., Org. Chem.: An Indian Journal, 2009, 5, 274).

Scheme 14

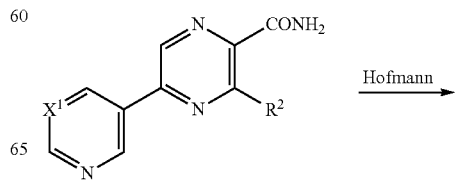

Hofmann

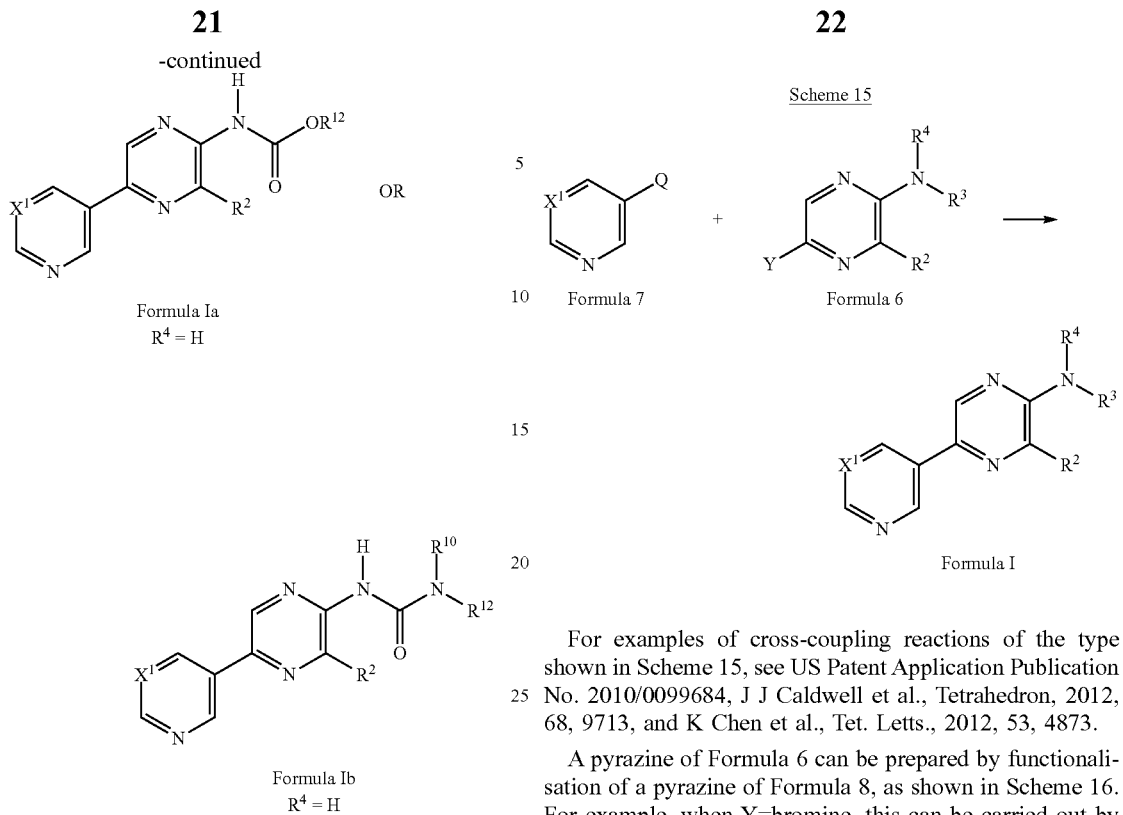

Formula Ia
R⁴ = H

Formula Ib
R⁴ = H

The first-formed product of the rearrangement is an isocyanate, but treatment with an alcohol of formula $R^{12}OH$, usually in the same reaction vessel, leads to a compound of the invention of Formula Ia in which $R^4$=H. Alternatively, the intermediate isocyanate can be hydrolysed to give the amino-pyrazine of Formula 4. The starting carboxamide shown in Scheme 7 can be prepared, for example, from the corresponding carboxylic acid via the acid chloride, or from the corresponding methyl or ethyl ester, or by partial hydrolysis of the corresponding cyanide.

Compounds of the invention of Formula Ib in which $R^4$=H can also be prepared by a Hofmann rearrangement, the first-formed isocyanate being treated with an amine of formula $R^{10}R^{12}NH$. For examples of reactions of this kind, see P Liu et al., Eur. J. Org. Chem., 2012, 1994.

A compound of the invention of Formula (I) can also be prepared by a cross-coupling reaction, as shown in Scheme 15. The cross-coupling partners can be a pyrazine of Formula 6, in which Y is chlorine, bromine, iodine or a pseudohalogen such as $OSO_2CF_3$, and a pyridine or pyrimidine of Formula 7, in which Q is the group $B(OR^Y)_2$ (this is preferred) or $Sn(R^Z)_3$ (in which $R^Y$=H or alkyl or the two groups $R^Y$ may join to form a ring, and $R^Z$=alkyl), in the presence of a suitable catalyst, usually a palladium catalyst, and optionally in the presence of a suitable ligand and/or a suitable base, and in a suitable solvent. Alternatively, the cross-coupling partners can be a pyrazine of Formula 6, in which Y is the group $B(OR^Y)_2$ (this is preferred) or $Sn(R^Z)_3$, and a pyridine or pyrimidine of Formula 7, in which Q is chlorine, bromine, iodine or a pseudohalogen such as $OSO_2CF_3$, in the presence of a suitable catalyst, usually a palladium catalyst, and optionally in the presence of a suitable ligand and/or a suitable base, and in a suitable solvent.

Scheme 15

Formula 7  +  Formula 6  →  Formula I

For examples of cross-coupling reactions of the type shown in Scheme 15, see US Patent Application Publication No. 2010/0099684, J J Caldwell et al., Tetrahedron, 2012, 68, 9713, and K Chen et al., Tet. Letts., 2012, 53, 4873.

A pyrazine of Formula 6 can be prepared by functionalisation of a pyrazine of Formula 8, as shown in Scheme 16. For example, when Y=bromine, this can be carried out by bromination using bromine or N-bromosuccinimide, or when Y=iodine, this can be carried out by iodination using iodine or N-iodosuccinimide, or when $Y=B(OR^Y)_2$ this can be carried out by reaction of the corresponding pyrazine in which Y=bromine or iodine with $(R^YO)_2B-B(OR^Y)_2$ under palladium catalysis, in a suitable solvent in each case. For an example of a bromination of this kind, see International Patent Publication No. WO 2010/071837.

Scheme 16

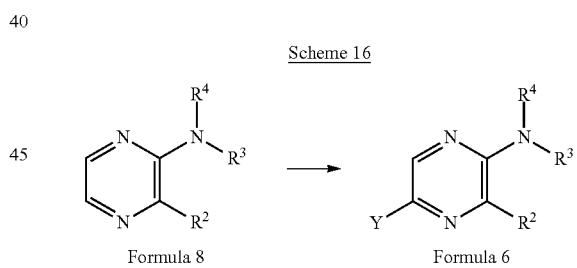

Formula 8     Formula 6

Pyridines and pyrimidines of Formula 7 are commercially available or can be made by methods described in the literature.

It will be understood by those skilled in the art that cross-coupling reactions of the types shown in Scheme 15 can also be carried out in a similar way on related pyrazines which, instead of $NR^3R^4$ and/or $R^2$, contain groups which are then converted into $NR^3R^4$ and/or $R^2$ after the cross-coupling reaction, using methods such as those shown in Schemes 1, 4, 5, 11, 13 and 14. The group $NR^3R^4$ may also be modified after cross-coupling, using methods such as those shown in Schemes 3 and 7.

In an alternative approach, a compound of Formula (I) can be prepared from a compound of Formula 9 by the method shown in Scheme 17.

Scheme 17

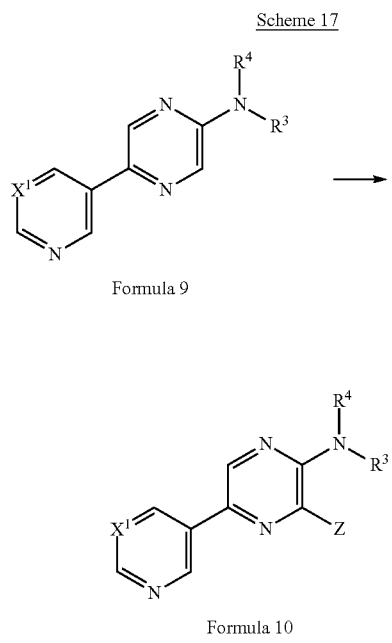

Formula 9

Formula 10

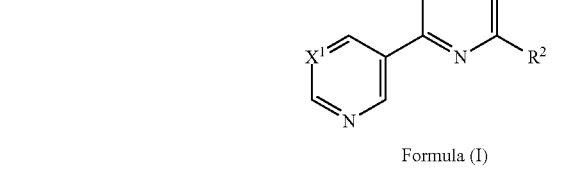

Formula (I)

In the first step, a group Z, which may be a halogen, alkylthio or nitro, is introduced directly to give a compound of Formula 10. For example, if Z=bromine, it can be introduced using bromine or N-bromosuccinimide, in a suitable solvent (see for example N Sato and R Takeuchi, Synthesis, 1990, 659). If Z is equal to a claimed value of $R^2$, this constitutes a way of directly introducing the group $R^2$ to prepare the corresponding compounds of the invention of Formula (I). Alternatively, the group Z can be converted in one or more steps by methods reported in the literature into the group $R^2$ to give a compound of the invention of Formula (I). For example, if the group Z is bromine, a substituent $R^2$ which is alkyl, cycloalkyl, alkenyl or aryl may be introduced by palladium-catalysed cross-coupling, and a substituent $R^2$ which is alkynyl may be introduced using a Sonogashira reaction, in a suitable solvent in each case.

Pyrazines of Formula 11, in which M is chlorine, bromine, iodine or a pseudohalogen such as $OSO_2CF_3$, and related compounds in which the group $NR^3R^4$ is replaced, for example, by $NH_2$ or NH-alkyl, can react regioselectively at the 3-position in displacement and cross-coupling reactions, as exemplified in Scheme 18. For example, the 3-bromo-group of 2-amino-3,5-dibromo-pyrazine is selectively displaced with alkoxides or secondary amines (see Examples 3-O and 3-P of International Patent Publication No. WO 2003/000666).

Scheme 18

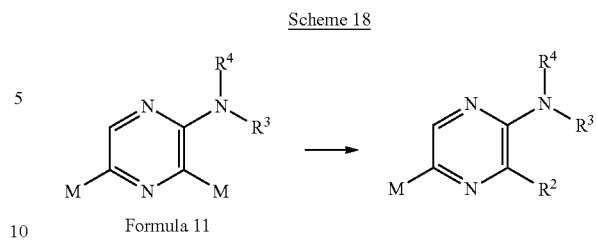

Formula 11

A compound of the invention of Formula (I) can also be prepared by approaches which involve the de novo synthesis of the pyrazine ring. A variety of such approaches have been reported in the literature. See, for example, Section 6.03.10 of Chapter 6.03, Pyrazines and their Benzo Derivatives, by N Sato, in Vol. 6 of Comprehensive Heterocyclic Chemistry II, Editors A R Katritzky, C W Rees and F V Scriven, Pergamon, 1996; N Sato, Science of Synthesis, 2004, 16, 751; and M P Cabal, Modern Heterocyclic Chemistry, 2011, 3, 1683. Representative examples of pyrazine ring syntheses are shown in Schemes 19 and 20 below.

Scheme 19 shows the reaction of a 1,2-diamine with an acyl cyanide which leads, following oxidation, to 2-amino-3-substituted-pyrazines (see, for example, R Lakhan and B J Rai, Synthesis, 1987, 914).

Scheme 19

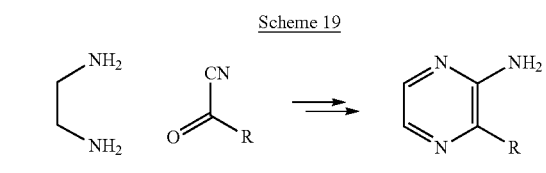

Scheme 20 shows a two-step approach to 3-substituted-5-aryl/heteroaryl-pyrazin-2-ones (see, for example, R H Bradbury et al., Heterocycles, 1990, 31, 1647). These pyrazin-2-ones can be converted, using methods reported in the literature, into the corresponding pyrazines with a group W at the 2-position, where W is a halogen, such as Cl, Br or I, or a group such as $OSO_2CF_3$. In turn, these pyrazines can be converted into compounds of the invention of Formula (I), as shown in Scheme 11.

Scheme 20

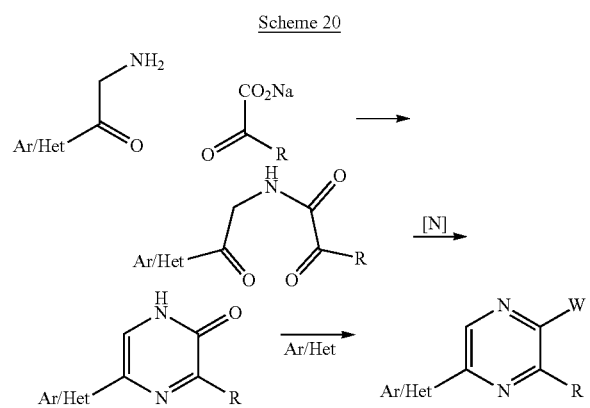

The compounds of Formula (I) as described herein may be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound as described herein and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

Such herbicidal compositions generally comprise from 0.1 to 99% by weight, especially from 0.1 to 95% by weight of compounds of Formula (I) and from 1 to 99.9% by weight of a formulation adjuvant, which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

Herbicidal compositions as described herein may further comprise at least one additional pesticide. For example, the compounds of formula (I) can also be used in combination with other herbicides or plant growth regulators. In a preferred embodiment the additional pesticide is a herbicide and/or herbicide safener. Examples of such mixtures are, in which ‘I’ represents a compound of Formula (I), I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halauxifen, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+tri-allate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6). The compounds of formula (I) and/or compositions of the present invention may also be combined with herbicidal compounds disclosed in WO06/024820 and/or WO07/096576.

The mixing partners of the compound of Formula (I) may also be in the form of esters or salts, as mentioned e.g. in The Pesticide Manual, Sixteenth Edition, British Crop Protection Council, 2012.

The compound of Formula (I) can also be used in mixtures with other agrochemicals such as fungicides, nematicides or insecticides, examples of which are given in The Pesticide Manual (supra).

The mixing ratio of the compound of Formula (I) to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula (I) as described herein can also be used in combination with one or more safeners. Likewise, mixtures of a compound of Formula (I) as described herein with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxybenzoylsulfamoyl)-benzamide (CAS RN 221668-34-4). Other possibilities include safener compounds disclosed in, for example, EP0365484 e.g N-(2-methoxybenzoyl)-4-[(methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[(methyl-aminocarbonyl)amino]benzenesulfonamide.

The safeners of the compound of Formula (I) may also be in the form of esters or salts, as mentioned e.g. in The Pesticide Manual (supra). The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula (I) to safener is from 100:1 to 1:10, especially from 20:1 to 1:1.

The mixtures can advantageously be used in the above-mentioned formulations (in which case "active ingredient" relates to the respective mixture of compound of Formula (I) with the safener).

As described above, compounds of formula (I) and/or compositions comprising such compounds may be used in methods of controlling unwanted plant growth, and in particular in controlling unwanted plant growth in crops of useful plants. Thus, the present invention further provides a method of selectively controlling weeds at a locus comprising crop plants and weeds, wherein the method comprises application to the locus, of a weed-controlling amount of a compound of formula (I), or a composition as described herein. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula (I) may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®, as well as those where the crop plant has been engineered to over-express homogentisate solanesyltransferase as taught in, for example, WO2010/029311.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate. Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled include both monocotyledonous (e.g. grassy) species, for example: *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria and Sorghum*; and dicotyledonous species, for example: *Abutilon, Amaranthus, Ambrosia, Chenopodium, Chrysanthemum, Conyza, Galium, Ipomoea, Kochia, Nasturtium, Polygonum, Sida, Sinapis, Solanum, Stellaria, Veronica, Viola* and *Xanthium*. Weeds can also include plants which may be considered crop plants but which are growing outside a crop area (escapes), or which grow from seed left over from a previous planting of a different crop (volunteers). Such volunteers or escapes may be tolerant to certain other herbicides.

Preferably the weeds to be controlled and/or growth-inhibited, include monocotyledonous weeds, more preferably grassy monocotyledonous weeds, in particular those from the following genus: *Agrostis, Alopecurus, Apera, Avena, Brachiaria, Bromus, Cenchrus, Cyperus* (a genus of sedges), *Digitaria, Echinochloa, Eleusine, Eriochloa, Fimbristylis* (a genus of sedges), *Juncus* (a genus of rushes), *Leptochloa, Lolium, Monochoria, Ottochloa, Panicum, Pennisetum, Phalaris, Poa, Rottboellia, Sagittaria, Scirpus* (a genus of sedges), *Setaria* and/or *Sorghum*, and/or volunteer corn (volunteer maize) weeds; in particular: *Alopecurus myosuroides* (ALOMY, English name "blackgrass"), *Apera spica-venti, Avena fatua* (AVEFA, English name "wild oats"), *Avena ludoviciana, Avena sterilis, Avena sativa* (English name "oats" (volunteer)), *Brachiaria decumbens, Brachiaria plantaginea, Brachiaria platyphylla* (BRAPP), *Bromus tectorum, Digitaria horizontalis, Digitaria insularis, Digitaria sanguinalis* (DIGSA), *Echinochloa crus-galli* (English name "common barnyard grass", ECHCG), *Echinochloa oryzoides, Echinochloa colona* or *colonum, Eleusine indica, Eriochloa villosa* (English name "woolly cup-grass"), *Leptochloa chinensis, Leptochloa panicoides, Lolium perenne* (LOLPE, English name "perennial ryegrass"), *Lolium multiflorum* (LOLMU, English name "Italian ryegrass"), *Lolium persicum* (English name "Persian darnel"), *Lolium rigidum, Panicum dichotomiflorum* (PANDI), *Panicum miliaceum* (English name "wild proso millet"), *Phalaris minor, Phalaris paradoxa, Poa annua* (POAAN, English name "annual bluegrass"), *Scirpus maritimus, Scirpus juncoides, Setaria viridis* (SETVI, English name "green foxtail"), *Setaria faberi* (SETFA, English name "giant foxtail"), *Setaria glauca, Setaria lutescens* (English name "yellow foxtail"), *Sorghum bicolor,* and/or *Sorghum halepense* (English name "Johnson grass"), and/or *Sorghum vulgare*; and/or volunteer corn (volunteer maize) weeds.

In one embodiment, grassy monocotyledonous weeds to be controlled comprise weeds from the genus: *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum*, and/or volunteer corn (volunteer maize) weeds; in particular: weeds from the genus *Agrostis, Alopecurus, Apera, Avena, Brachiaria, Bromus, Cenchrus, Digitaria, Echinochloa, Eleusine, Eriochloa, Leptochloa, Lolium, Panicum, Phalaris, Poa, Rottboellia, Setaria,* and/or *Sorghum*, and/or volunteer corn (volunteer maize) weeds.

In a further embodiment, the grassy monocotyledonous weeds are "warm-season" (warm climate) grassy weeds; in which case they preferably comprise (e.g. are): weeds from the genus *Brachiaria, Cenchrus, Digitaria, Echinochloa, Eleusine, Eriochloa, Leptochloa, Ottochloa, Panicum, Pennisetum, Phalaris, Rottboellia, Setaria* and/or *Sorghum*, and/or volunteer corn (volunteer maize) weeds. More preferably, the grassy monocotyledonous weeds, e.g. to be controlled and/or growth-inhibited, are "warm-season" (warm climate) grassy weeds comprising (e.g. being): weeds from the genus *Brachiaria, Cenchrus, Digitaria, Echinochloa, Eleusine, Eriochloa, Panicum, Setaria* and/or *Sorghum*, and/or volunteer corn (volunteer maize) weeds.

In another particular embodiment the grassy monocotyledonous weeds, are "cool-season" (cool climate) grassy weeds; in which case they typically comprise weeds from the genus *Agrostis, Alopecurus, Apera, Avena, Bromus, Lolium* and/or *Poa*.

Various aspects and embodiments of the present invention will now be illustrated in more detail by way of example. Novel methodology and intermediates described therein are considered yet further aspects of the invention. It will be appreciated that modification of detail may be made without departing from the scope of the invention.

EXAMPLES

Preparation Examples

Those skilled in the art will appreciate that depending on the nature of the substituents $X^1$, $X^2$, $X^3$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^a$, $R^b$, $R^c$, n, p, q r and s, compounds of Formula (I) may exist in different interconvertible rotameric forms as described in, for example S. A. Richards and J. C. Hollerton, Essential Practical NMR for Organic Chemistry, John Wiley and sons (2010). For clarity, only the spectroscopic data for the major rotameric form is quoted.

Example P1: Preparation of 2-bis(tert-butoxycarbonyl)amino-3-methyl-5-(5-fluoropyrid-3-yl)pyrazine (H2)

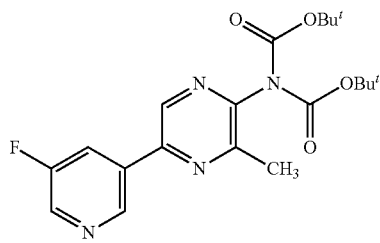

Step 1: Preparation of 2-bis(tert-butoxycarbonyl)amino-3-methyl-5-(5-fluoropyrid-3-yl)pyrazine (H2)

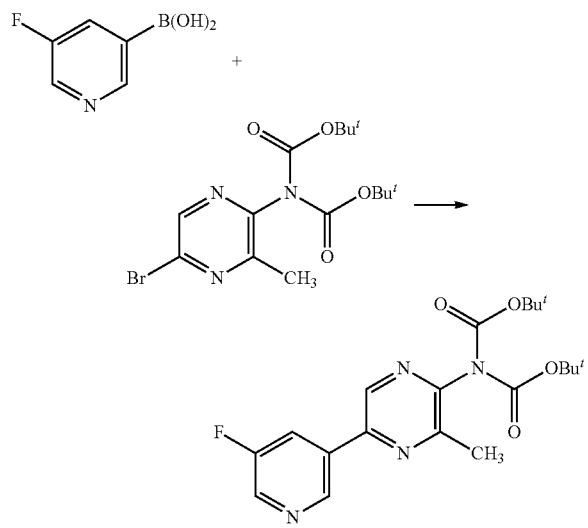

2-Bis-(tert-butoxycarbonyl)amino-3-methyl-5-bromopyrazine (1.50 g, 3.86 mmol), (5-fluoro-3-pyridyl)boronic acid (0.79 g, 5.4 mmol) and cesium carbonate (3.15 g, 9.7 mmol) were dissolved in a mixture of 1,4-dioxane (40 ml) and water (8 ml) and [1,1-bis(diphenylphosphino)ferrocene]-dichloropalladium(11) (160 mg, 0.22 mmol) was added. The resulting mixture was heated under reflux for 15 minutes, then allowed to cool, diluted with ethyl acetate (100 ml) and washed with water. The resulting organic solution was dried over magnesium sulfate then filtered and concentrated under reduced pressure to give a light brown oil (2.1 g) which was purified by chromatography on silica gel using a gradient of ethyl acetate in isohexane as eluent to give the title compound (1.32 g, 84% yield) as a white solid.

$^1$H NMR (400 MHz CDCl$_3$) δ 9.10; (s, 1H), 8.80; (s, 1H), 8.60; (d, 1H), 8.15; (dd, 1H), 2.60; (s, 3H), 1.40; (s, 18H).

Example P2: Preparation of tert-butyl N-(3-methyl-5-(5-fluoropyridin-3-yl)-pyrazin-2-yl)-N-methyl-carbamate (H19)

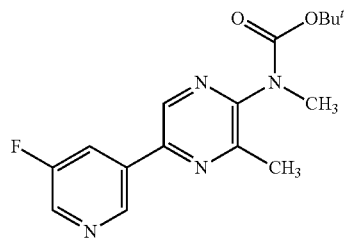

Step 1: Preparation of tert-butyl N-(3-methyl-5-(5-fluoropyridin-3-yl)-pyrazin-2-yl)-N-methyl-carbamate (H19)

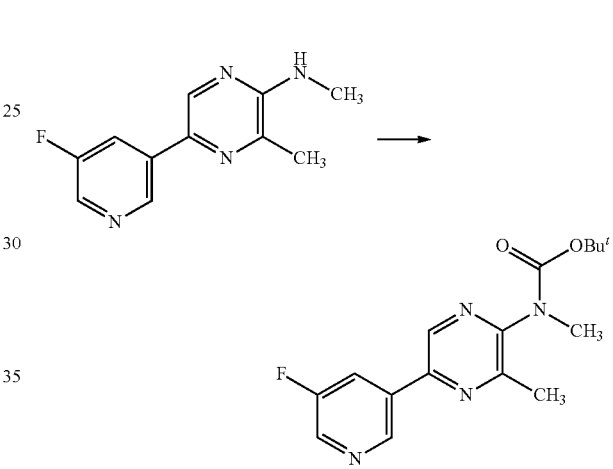

A solution of tert-butoxycarbonyl tert-butyl carbonate (610 mg, 2.8 mmol) in dichloromethane (1 ml) was added dropwise to a stirred solution of 5-(5-fluoro-3-pyridyl)-N,3-dimethyl-pyrazin-2-amine (400 mg, 1.8 mmol) and 4-dimethylaminopyridine (11 mg, 0.09 mmol) in dichloromethane (15 ml) at room temperature. The resulting mixture was stirred at room temperature for 48 hours and then purified by chromatography on silica gel using a gradient of ethyl acetate in isohexane as eluent to give tert-butyl N-(3-methyl-5-(5-fluoropyridin-3-yl)-pyrazin-2-yl)-N-methyl-carbamate (210 mg, 31% yield) as a viscous oil.

$^1$H NMR 400 MHz CDCl$_3$ δ 9.05; (s, 1H), 8.75; (s, 1H), 8.55; (s, 1H), 8.10; (dd, 1H), 3.30; (s, 3H), 2.60; (s, 3H), 1.45; (s, 9H).

Example P3: Preparation of 5-(5-fluoro-3-pyridyl)-3-isopropenyl-pyrazin-2-amine (Compound G14)

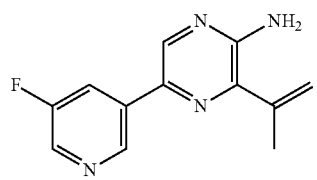 [SMILES: C=C(C)c1nc(-c2cncc(F)c2)cnc1N]

Step 1: Preparation of 2-amino-3-(prop-2-enyl)-5-bromopyrazine

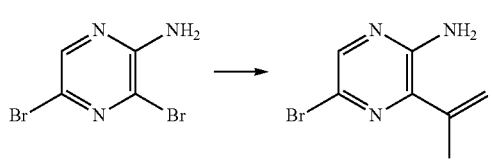

4,4,5,5-Tetramethyl-2-(prop-2-enyl)-1,3,2-dioxaborolane (4.9 g, 27 mmol), cesium carbonate (20 g, 62 mmol), water (16 ml) and [1,1'-bis(diphenylphosphino)ferrocene]-dichloropalladium(II) (960 mg, 1.2 mmol) were added to a stirred solution of 2-amino-3,5-dibromopyrazine (6.5 g, 25 mmol) in 1,4-dioxane (65 ml) at room temperature. The resulting mixture was heated under reflux for 3 hours, allowed to cool, and then concentrated under reduced pressure. Water was added to the resulting red residue, and the resulting mixture was extracted with ethyl acetate. The extracts were washed with brine, dried over magnesium sulfate, then filtered and concentrated under reduced pressure to give a red oil. Purification was achieved by chromatography, first on silica gel using a gradient of ethyl acetate in isohexane as eluent, and then by mass-directed reverse phase HPLC to give the title compound (1.3 g, 24%) as a fluffy white solid.

$^1$H NMR (400 MHz, CDCl$_3$) δ 8.15; (s, 1H), 5.75; (s, 1H), 5.20; (s, 1H), 5.15; (br s, 2H), 2.15; (s, 3H).

Step 2: Preparation of 5-(5-fluoro-3-pyridyl)-3-isopropenyl-pyrazin-2-amine (Compound G14)

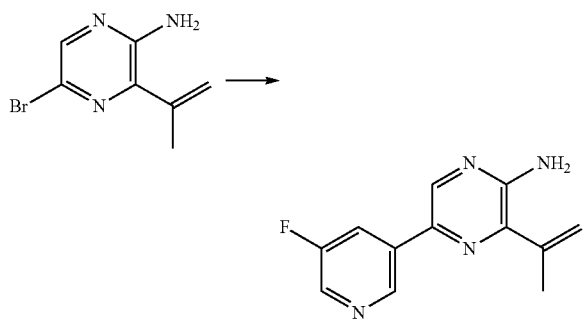

2-Amino-3-(prop-2-enyl)-5-bromopyrazine (428 mg, 2.00 mmol), (5-fluoro-3-pyridyl)boronic acid (411 mg, 2.80 mmol) and cesium carbonate (1.63 g, 5.00 mmol) were dissolved in a mixture of 1,4-dioxane (4.5 ml) and water (1 ml), and [1,1-bis(diphenylphosphino)ferrocene]-dichloropalladium(II) (85 mg, 0.11 mmol) was added. The resulting mixture was heated under reflux for 3 hours, then allowed to cool, diluted with ethyl acetate (100 ml), and then washed with brine. The resulting organic solution was dried over magnesium sulfate then filtered and concentrated under reduced pressure to give 2 a dark yellow liquid which began to crystallize. This was purified by chromatography on silica gel using a gradient of ethyl acetate in isohexane as eluent to give the title compound (400 mgs, 86%) as a yellow solid.

$^1$H NMR (400 MHz, CDCl$_3$) δ 8.95; (s, 1H), 8.45; (d, 1H), 8.40; (s, 1H), 8.00; (dd, 1H), 5.60; (s, 1H), 5.55; (s, 1H) 5.10; (br s, 2H), 2.25; (s, 3H).

Example P4: Preparation of 2-amino-3-(prop-2-yl)-5-(5-fluoropyrid-3-yl)pyrazine

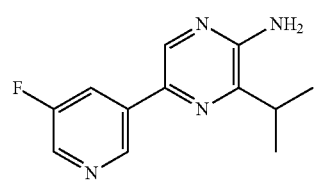 [SMILES: CC(C)c1nc(-c2cncc(F)c2)cnc1N]

Step 1: Preparation of 2-amino-3-(prop-2-yl)-5-(5-fluoropyrid-3-yl)pyrazine (Compound G15)

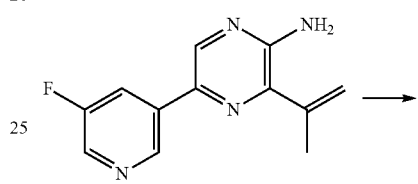

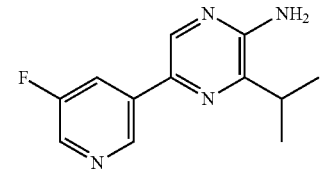

5% Palladium on carbon (55% water, 10 mg, 0.09 mmol) was added to a stirred solution of 2-amino-3-(prop-2-enyl)-5-(5-fluoropyrid-3-yl)pyrazine (300 mg, 1.30 mmol) in ethanol (10 ml) and the resulting mixture was put under an atmosphere of hydrogen (1.5 bar). After 2 hours, the reaction was stopped and the reaction mixture was purged with nitrogen, then filtered and concentrated under reduced pressure to give the title compound (280 mg, 93%) as a fluffy white solid. $^1$H NMR (400 MHz, CDCl$_3$) δ 9.00; (s, 1H), 8.45; (s, 1H), 8.35; (s, 1H), 8.00; (dd, 1H), 4.75; (br s, 2H), 2.95; (m, 1H), 1.35; (d, 6H).

Example P5: Preparation of 2-bis-(tert-butoxycarbonyl)amino-3,5-dibromopyrazine

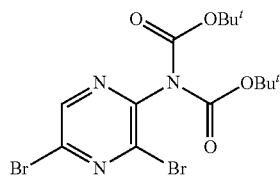

Step 1: Preparation of 2-bis-(tert-butoxycarbonyl) amino-3,5-dibromopyrazine

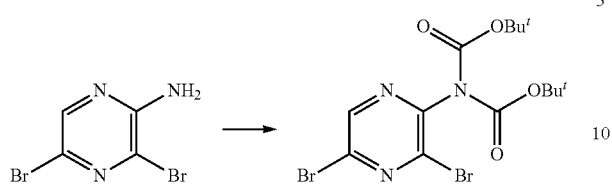

4-Dimethylaminopyridine (61 mg, 0.49 mmol) was added to a stirred solution of 2-amino-3,5-dibromopyrazine (2.5 g, 9.8 mmol) in dichloromethane (50 ml) at room temperature. A solution of tert-butoxycarbonyl tert-butyl carbonate (5.4 g, 24 mmol) in dichloromethane (10 ml) was then added dropwise with stirring over 10 minutes. The resulting mixture was stirred at room temperature for an hour then concentrated under reduced pressure to give 2-bis-(tert-butoxycarbonyl)amino-3,5-dibromopyrazine (4.3 g, 95% yield) as a beige solid.

$^1$H NMR (400 MHz, CDCl$_3$) δ 8.45; (s, 1H), 1.40; (s, 18H).

Example P6: Preparation of 2-amino-3-bromo-5-(5-fluoropyrid-3-yl)pyrazine

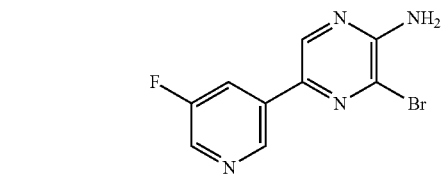 [SMILES: Nc1ncc(-c2cncc(F)c2)nc1Br]

Step 1: Preparation of 2-amino-3-bromo-5-(5-fluoropyrid-3-yl)pyrazine

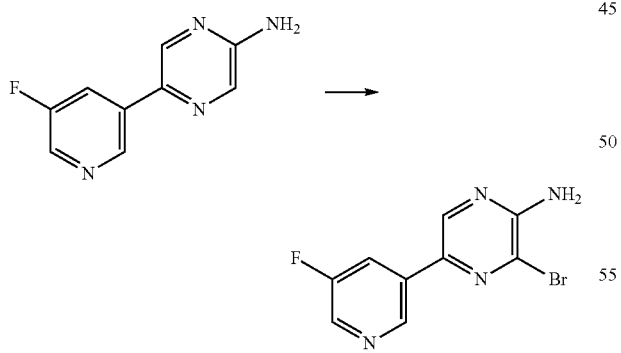

Bromine (0.20 ml, 3.8 mmol) was added dropwise to a stirred solution of 2-amino-(5-fluoropyrid-3-yl)pyrazine (600 mg, 3.2 mmol) and pyridine (300 mg, 3.8 mmol) in 1,4-dioxane (30 ml) and the resulting mixture was stirred at room temperature for one hour. The mixture was diluted with ethyl acetate (100 ml) then washed with aqueous sodium bicarbonate and then aqueous sodium metabisulfite, dried over magnesium sulfate and concentrated under reduced pressure. The residue was purified by chromatography on silica gel using a gradient of ethyl acetate in hexane as eluent to give 2-amino-3-bromo-5-(5-fluoropyrid-3-yl) pyrazine (160 mg, 19%) as a yellow solid. $^1$H NMR (400 MHz, CDCl$_3$)δ 8.95; (s, 1H), 8.55; (s, 1H), 8.45; (s, 1H), 8.15; (dd, 1H),

Example P7: Preparation of tert-butyl N-(5-bromo-3-methyl-pyrazin-2-yl)-carbamate

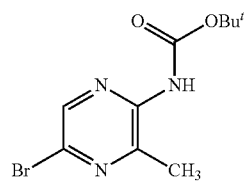

Step 1: Preparation of tert-butyl N-(3-methyl-pyrazin-2-yl)-carbamate

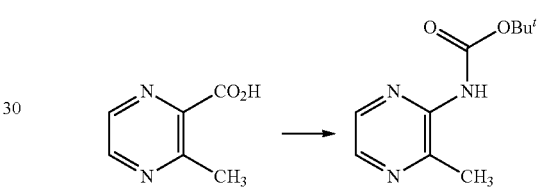

Diphenylphosphoryl azide (22.2 g, 80.5 mmol) was added to a stirred solution of 3-methylpyrazine-2-carboxylic acid (9.0 g, 61.9 mmol) in toluene (90 ml), tert-butanol (45 ml) and triethylamine (8.18 g, 80.5 mmol). The resulting mixture was heated at 90° C. for 4 hours (reaction was observed to begin during heating, at about 65° C. internal temperature) and then allowed to cool. The solvent was removed under reduced pressure and the residue was re-dissolved in ethyl acetate (150 m). The resulting solution was washed with 2M aqueous sodium bicarbonate then dried using a phase separation membrane, concentrated under reduced pressure and purified by chromatography on silica gel using a gradient of ethyl acetate in hexane as eluent to give tert-butyl N-(3-methyl-pyrazin-2-yl)-carbamate (8.0 g, 59%) as a colourless oil which slowly crystallised. $^1$H NMR (400 MHz, CDCl$_3$) δ 8.27; (d, 1H), 8.23; (d, 1H), 6.85; (br s, 1H), 1.53; (s, 9H).

Step 2: Preparation of tert-butyl N-(5-bromo-3-methyl-pyrazin-2-yl)-carbamate

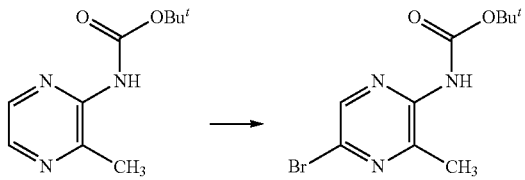

Bromine (127 mg, 0.79 mmol) was added dropwise at room temperature to a stirred solution of tert-butyl N-(3- methyl-pyrazin-2-yl)-carbamate (150 mg, 0.72 mmol) and pyridine (69 mg, 0.86 mmol) in chloroform (4.5 ml). The resulting mixture was stirred at room temperature for 24 hours and then concentrated under reduced pressure. The residue was dissolved in dichloromethane (10 ml), washed with water, dried using a phase-separation membrane and purified by chromatography on silica gel using mixtures of ethyl acetate and hexane as eluent to give tert-butyl N-(5-bromo-3-methyl-pyrazin-2-yl)-carbamate as a white solid (140 mg, 68%).

$^1$H NMR (400 MHz, CDCl$_3$) δ 8.30; (s, 1H), 6.65; (br s, 1H), 2.55; (s, 3H), 1.55; (s, 9H).

Example P8: Preparation of 3-trifluoromethyl-2-aminopyrazine

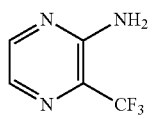

Step 1: Preparation of tert-butyl N-(3-trifluoromethylpyrazin-2-yl)-carbamate

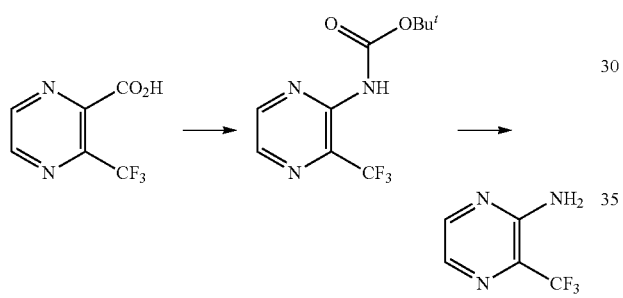

Diphenylphosphoryl azide (3.47 g, 12.6 mmol) was added to a stirred solution of 3-trifluoromethylpyrazine-2-carboxylic acid (1.92 g, 9.70 mmol) and triethylamine (1.28 g, 12.6 mmol) in tert-butanol (9.6 ml, 100 mmol) and toluene (19.2 ml). The resulting mixture was heated at 90° C. for 4 hours and then allowed to cool. It was washed with 2M aqueous sodium bicarbonate, then dried through a phase-separation filter and concentrated under reduced pressure. The residue was purified by chromatography on silica gel using a gradient of ethyl acetate in hexane as eluent to give tert-butyl N-(3-trifluoromethylpyrazin-2-yl)-carbamate (2.0 g) as a colourless oil which slowly crystallised to give a white solid. $^1$H NMR (400 MHz, CDCl$_3$)δ 8.70; (s, 1H), 8.40; (s, 1H), 7.20; (br s, 1H), 1.55; (s, 9H).

Step 2: Preparation of 3-trifluoromethyl-2-aminopyrazine

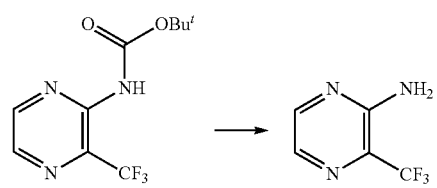

Trifluoroacetic acid (1.1 ml, 14 mmol) was added in portions to a stirred solution of tert-butyl N-(3-trifluoromethylpyrazin-2-yl)-carbamate (0.92 g, ca. 3.5 mmol) in 1,2-dichlorethane (9.2 ml) at room temperature. The resulting mixture was heated under reflux for 2 hours, allowed to cool, then washed with saturated aqueous sodium bicarbonate and dried through a phase-separation filter. Concentration under reduced pressure then gave 3-trifluoromethyl-2-aminopyrazine (0.48 g) as a yellow solid. $^1$H NMR (400 MHz, CDCl$_3$) δ 8.25; (s, 1H), 8.00; (s, 1H), 5.15; (br s, 1H).

Example P9: Preparation of tert-butyl N-(3-methyl-pyrazin-2-yl)-N-methyl-carbamate

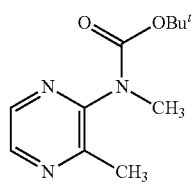

Step 1: Preparation of tert-butyl N-(3-methyl-pyrazin-2-yl)-N-methyl-carbamate

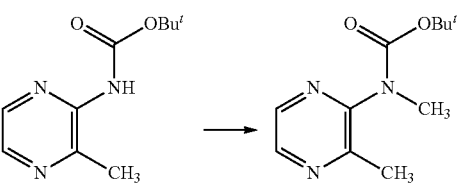

A solution of tert-butyl N-(3-methyl-pyrazin-2-yl)-carbamate (1.05 g, 5.0 mmol) in dry DMF was added dropwise to a stirred suspension of sodium hydride (220 mg, 5.5 mmol) in dry DMF at room temperature (total volume of DMF ~10 ml). The resulting mixture was stirred at room temperature for 30 minutes, then methyl iodide (3.6 g, 25 mmol) was added in one portion. The reaction mixture was stirred for 2 hours, then quenched with water and extracted with ethyl acetate. The extracts were washed with water and brine, then dried over magnesium sulfate and concentrated under reduced pressure. The residue was purified mass directed reverse phase HPLC to give tert-butyl N-(3-methyl-pyrazin-2-yl)-N-methyl-carbamate (24 mg, 2%) as an oil. $^1$H NMR (400 MHz, CDCl$_3$) δ 7.35; (d, 1H), 7.00; (d, 1H), 3.55; (s, 3H), 2.50; (s, 3H), 1.55; (s, 9H).

Example P10: Preparation of ethyl 3-difluoromethylpyrazine-2-carboxylate

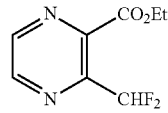

Step 1: Preparation of ethyl 2-chloro-4,4-difluoroacetoacetate

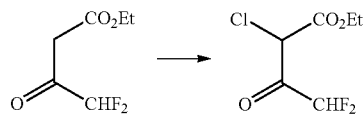

Sulfuryl chloride (14.9 g, 0.11 mol) was added dropwise to ethyl 4,4-difluoroacetoacetate (16.6 g, 0.1 mol) with stirring at room temperature. After the addition, the solution was stirred for 12 h., then distilled to give ethyl 2-chloro-4,4-difluoroacetoacetate (17.1 g, 85% yield) as a colourless liquid.

$^1$H NMR (400 MHz, CDCl$_3$) δ 11.79; (t, 1H), 5.75-6.16; (m, 0.5H), 5.49; (s, 0.5H), 4.2-4.34; (m, 2H), 1.27-1.39; (m, 3H).

Step 2: Preparation of ethyl 3-difluoromethylpyrazine-2-carboxylate

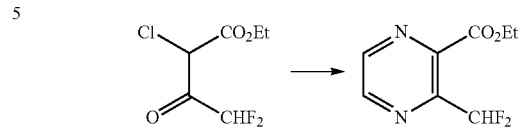

Pd/C (10 g, 5%) was added to a mixture of ethyl 2-chloro-4,4-difluoroaceto-acetate (10 g, 50 mmol), sodium azide (7.8 g, 120 mmol) and 1,2-ethanediamine dihydrochloride (7.98 g, 60 mmol) in water (30 ml) and ethyl acetate (100 ml) at 30° C., and the resulting mixture was heated under reflux for 3 h. After cooling to room temperature, the reaction mixture was filtered and extracted with ethyl acetate (3×100 ml). The combined extracts were washed with brine, dried over MgSO$_4$ and evaporated under reduced pressure. The residue was purified by column chromatography on silica gel using petroleum ether/ethyl acetate=3:1 as eluent to give ethyl 3-difluoromethyl-pyrazine-2-carboxylate (3.0 g, 30%) as a yellow oil. $^1$H NMR (400 MHz, CDCl$_3$) δ 8.86; (d, 2H), 7.41; (t, 1H), 4.54; (q, 2H), 1.48; (t, 3H).

Further examples of the invention can be prepared similarly using the methods described above. Table 2 below, shows the structure of these compounds and the physical characterising data obtained using one or more of methods as outlined below.

TABLE 2

Characterising data for compounds of Formula (I) made by the methods described above.

| Compound ID | Structure | Data (400 MHz, CDCl$_3$) unless stated |
|---|---|---|
| H1 | 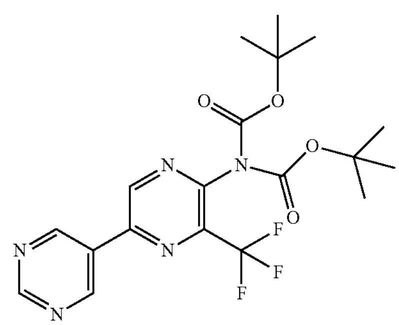 [SMILES: CC(C)(C)OC(=O)N(C(=O)OC(C)(C)C)c1ncc(-c2cncnc2)nc1C(F)(F)F] | 9.50 (s, 2H), 9.40 (s, 1H), 9.20 (s, 1H), 1.40 (s, 18H) |
| H2 | 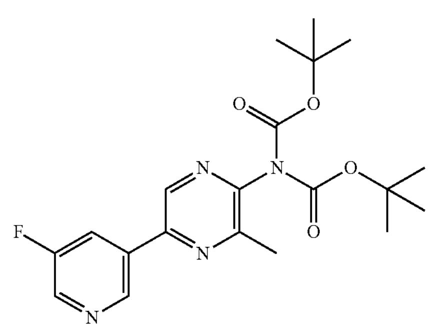 [SMILES: Cc1nc(-c2cncc(F)c2)cnc1N(C(=O)OC(C)(C)C)C(=O)OC(C)(C)C] | 9.10 (s, 1H), 8.80 (s, 1H), 8.60 (d, 1H), 8.15 (dd, 1H), 2.60 (s, 3H), 1.40 (s, 18H) |

TABLE 2-continued

Characterising data for compounds of Formula (I) made by the methods described above.

| Compound ID | Structure | Data (400 MHz, CDCl₃) unless stated |
|---|---|---|
| H3 | 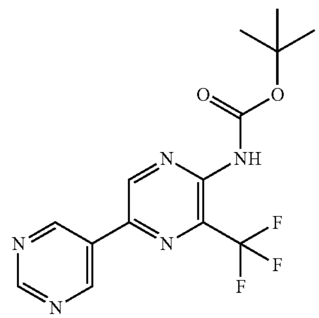 [SMILES: CC(C)(C)OC(=O)Nc1ncc(-c2cncnc2)nc1C(F)(F)F] | 9.35 (s, 2H), 9.30 (s, 1H), 9.05 (s, 1H), 7.30 (br s, 1H), 1.60 (s, 9H) |
| H4 | 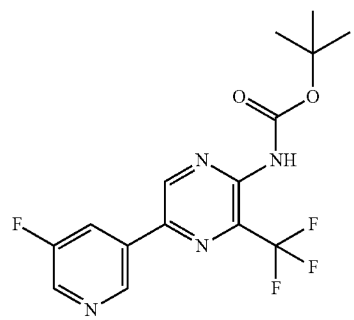 [SMILES: CC(C)(C)OC(=O)Nc1ncc(-c2cncc(F)c2)nc1C(F)(F)F] | 9.1 (s, 1H), 9.05 (s, 1H), 8.60 (s, 1H), 8.10 (dd, 1H), 1.55 (s, 9H) |
| H5 | 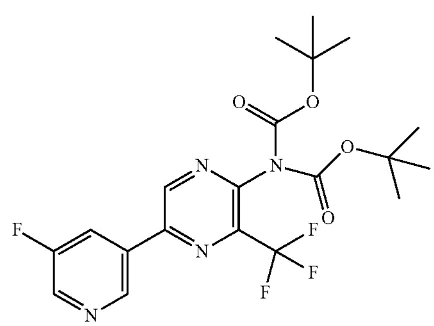 [SMILES: CC(C)(C)OC(=O)N(C(=O)OC(C)(C)C)c1ncc(-c2cncc(F)c2)nc1C(F)(F)F] | 9.20 (s, 1H), 9.15 (s, 1H), 8.65 (s, 1H), 8.20 (dd, 1H), 1.40 (s, 18H) |
| H6 | 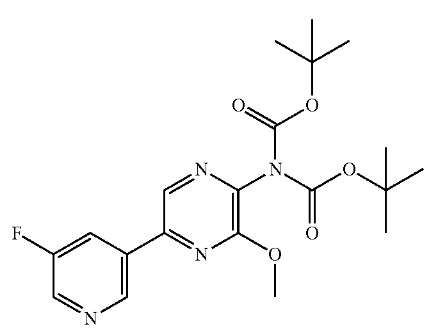 [SMILES: COc1nc(-c2cncc(F)c2)cnc1N(C(=O)OC(C)(C)C)C(=O)OC(C)(C)C] | 9.10 (s, 1H), 8.60 (s, 1H), 8.50 (s, 1H), 8.10 (dd, 1H), 4.15 (s, 3H), 1.40 (s, 18H) |

TABLE 2-continued
Characterising data for compounds of Formula (I) made by the methods described above.
| Compound ID | Structure | Data (400 MHz, CDCl$_3$) unless stated |
|---|---|---|
| H7 | 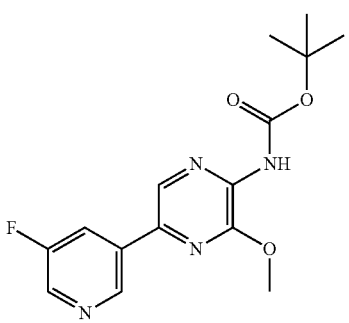 [SMILES: COc1nc(-c2cncc(F)c2)cnc1NC(=O)OC(C)(C)C] | 9.00 (s, 1H), 8.50 (s, 1H), 8.45 (s, 1H), 7.95 (dd, 1H). 7.50 (br s, 1H), 4.15 (s, 3H), 1.60 (s, 9H) |
| H8 | 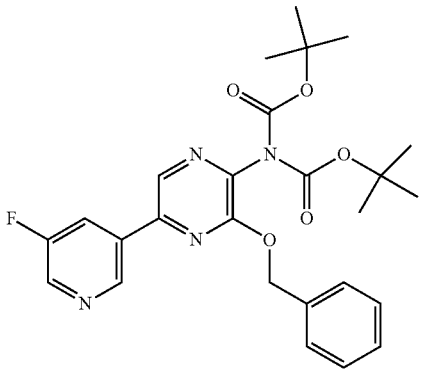 [SMILES: CC(C)(C)OC(=O)N(C(=O)OC(C)(C)C)c1ncc(-c2cncc(F)c2)nc1OCc1ccccc1] | 9.10 (s, 1H), 8.60 (s, 1H), 8.50 (s, 1H), 8.00 (dd, 1H), 7.45 (m, 2H), 7.35 (m, 3H), 5.55 (s, 2H), 1.40 (s, 18H) |
| H9 | 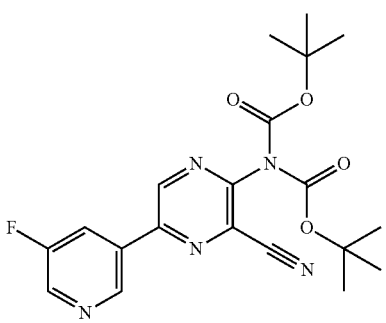 [SMILES: CC(C)(C)OC(=O)N(C(=O)OC(C)(C)C)c1ncc(-c2cncc(F)c2)nc1C#N] | 9.20 (s, 1H), 9.10 (s, 1H), 8.65 (d, 1H), 8.15 (dd, 1H), 1.50 (s, 18H) |
| H10 | 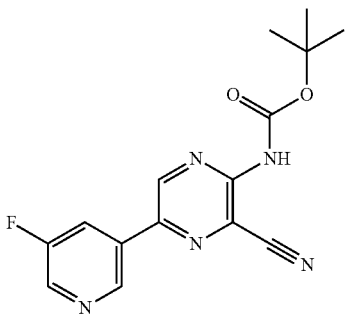 [SMILES: CC(C)(C)OC(=O)Nc1ncc(-c2cncc(F)c2)nc1C#N] | 9.00 (s, 2H), 8.60 (d, 1H), 8.10 (dd, 1H), 7.45 (dd, 1H), 1.60 (s, 9H) |

TABLE 2-continued

Characterising data for compounds of Formula (I) made by the methods described above.

| Compound ID | Structure | Data (400 MHz, CDCl₃) unless stated |
|---|---|---|
| H11 | 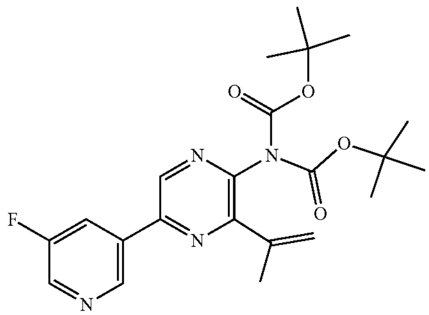 [SMILES: C=C(C)c1nc(-c2cncc(F)c2)cnc1N(C(=O)OC(C)(C)C)C(=O)OC(C)(C)C] | 9.10 (s, 1H), 8.85 (s, 1H), 8.60 (d, 1H), 8.15 (dd, 1H), 5.55 (s, 2H), 2.25 (s, 3H), 1.45 (s, 18H) |
| H12 | 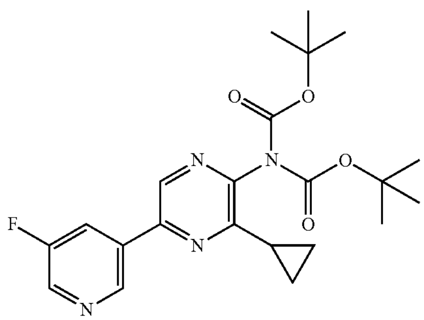 [SMILES: CC(C)(C)OC(=O)N(C(=O)OC(C)(C)C)c1ncc(-c2cncc(F)c2)nc1C1CC1] | 9.05 (s, 1H), 8.70 (s, 1H), 8.55 (d, 1H), 8.05 (dd, 1H), 2.20-2.10 (m, 1H), 1.45 (s, 18H), 1.30-1.20 (m, 2H), 1.15-1.05 (m, 2H) |
| H13 | 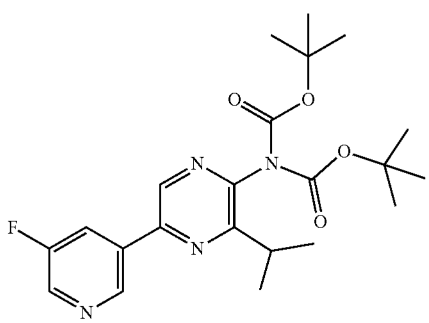 [SMILES: CC(C)c1nc(-c2cncc(F)c2)cnc1N(C(=O)OC(C)(C)C)C(=O)OC(C)(C)C] | 9.15 (s, 1H), 8.8 (s, 1H), 8.60 (d, 1H), 8.20 (dd, 1H), 3.25-3.15 (m, 1H), 1.45 (s, 18H), 1.35 (d, 6H) |
| H14 | 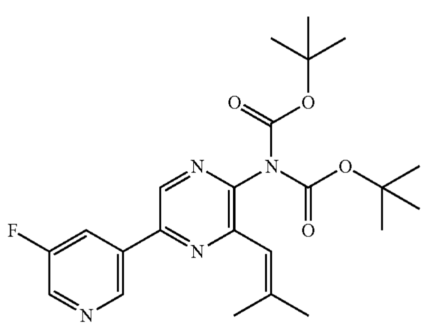 [SMILES: CC(C)=Cc1nc(-c2cncc(F)c2)cnc1N(C(=O)OC(C)(C)C)C(=O)OC(C)(C)C] | 9.10 (s, 1H), 8.75 (s, 1H), 8.60 (d, 1H), 8.10 (dd, 1H), 6.30 (s, 1H), 2.25 (s, 3H), 2.05 (s, 3H), 1.40 (s, 18H) |

TABLE 2-continued

Characterising data for compounds of Formula (I) made by the methods described above.

| Compound ID | Structure | Data (400 MHz, CDCl₃) unless stated |
|---|---|---|
| H15 | 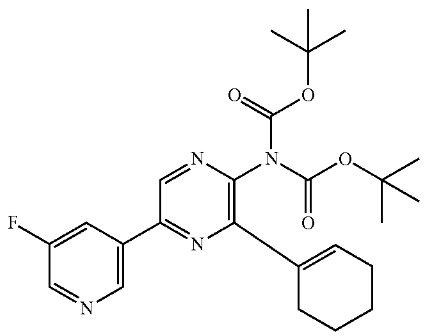 [SMILES: CC(C)(C)OC(=O)N(C(=O)OC(C)(C)C)c1ncc(-c2cncc(F)c2)nc1C1=CCCCC1] | 9.10 (s, 1H), 8.80 (s, 1H), 8.55 (d, 1H), 8.15 (dd, 1H), 6.35 (t, 1H), 2.60-2.50 (m, 2H), 2.30-2.20 (m, 2H), 1.85-1.75 (m, 2H), 1.75-1.65 (m, 2H), 1.45 (s, 18H) |
| H16 | 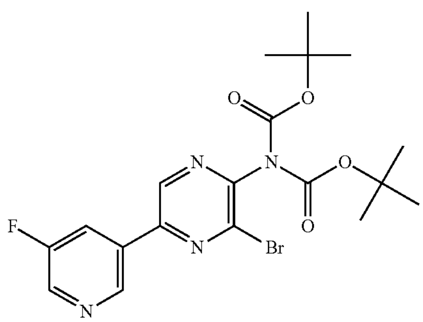 [SMILES: CC(C)(C)OC(=O)N(C(=O)OC(C)(C)C)c1ncc(-c2cncc(F)c2)nc1Br] | 9.10 (s, 1H), 8.90 (s, 1H), 8.60 (d, 1H), 8.15 (dd, 1H), 1.45 (s, 18H) |
| H17 | 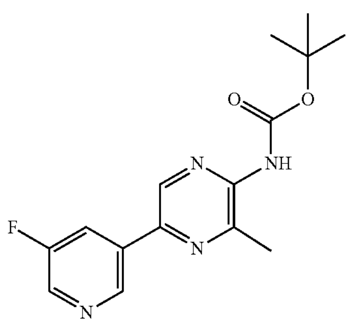 [SMILES: Cc1nc(-c2cncc(F)c2)cnc1NC(=O)OC(C)(C)C] | 9.00 (s, 1H), 8.70 (s, 1H), 8.50 (s, 1H), 8.05 (dd, 1H), 6.80 (br s, 1H), 2.60 (s, 3H), 1.55 (s, 9H) |
| H18 | 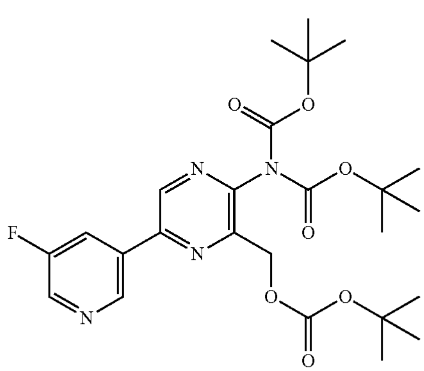 [SMILES: CC(C)(C)OC(=O)OCc1nc(-c2cncc(F)c2)cnc1N(C(=O)OC(C)(C)C)C(=O)OC(C)(C)C] | 9.10 (s, 1H), 8.95 (s, 1H), 8.60 (s, 1H), 8.15 (dd, 1H), 5.25 (s, 2H), 1.55 (s, 9H), 1.45 (s, 18H) |

TABLE 2-continued

Characterising data for compounds of Formula (I) made by the methods described above.

| Compound ID | Structure | Data (400 MHz, CDCl$_3$) unless stated |
| --- | --- | --- |
| H19 | 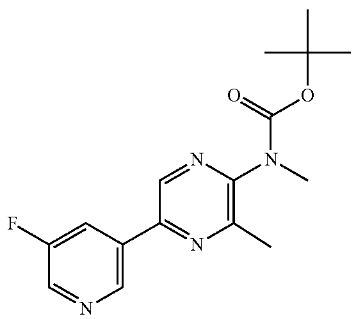 [SMILES: Cc1nc(-c2cncc(F)c2)cnc1N(C)C(=O)OC(C)(C)C] | 9.05 (s, 1H), 8.75 (s, 1H), 8.55 (s, 1H), 8.10 (dd, 1H), 3.30 (s, 3H), 2.60 (s, 3H), 1.45 (s, 9H) |
| H20 | 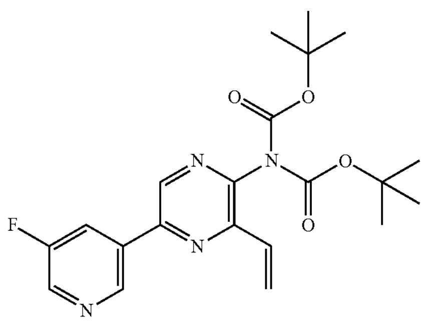 [SMILES: C=Cc1nc(-c2cncc(F)c2)cnc1N(C(=O)OC(C)(C)C)C(=O)OC(C)(C)C] | 9.15 (s, 1H), 8.85 (s, 1H), 8.60 (d, 1H), 8.20 (dd, 1H), 6.90 (dd, 1H), 6.70 (dd, 1H), 5.75 (dd, 1H), 1.40 (s, 18H) |
| H21 | 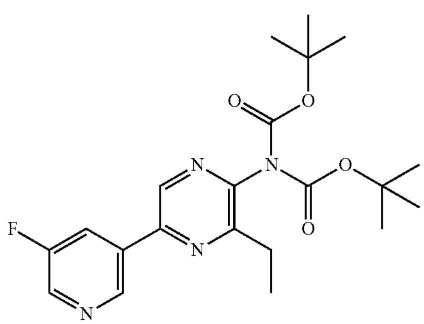 [SMILES: CCc1nc(-c2cncc(F)c2)cnc1N(C(=O)OC(C)(C)C)C(=O)OC(C)(C)C] | 9.10 (s, 1H), 8.80 (s, 1H), 8.55 (d, 1H), 8.15 (dd, 1H), 2.85 (q, 2H), 1.45 (s, 18H), 1.35 (t, 3H) |
| H22 | 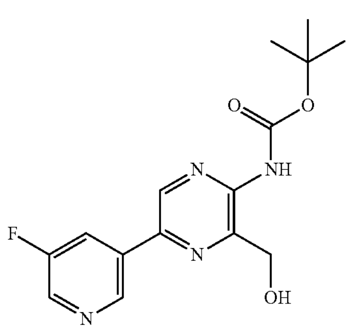 [SMILES: CC(C)(C)OC(=O)Nc1ncc(-c2cncc(F)c2)nc1CO] | 8.95 (s, 1H), 8.55 (s, 1H), 8.45 (d, 1H), 8.00 (dd, 1H), 5.35 (br s, 2H), 1.50 (s, 9H) |

TABLE 2-continued

Characterising data for compounds of Formula (I) made by the methods described above.

| Compound ID | Structure | Data (400 MHz, CDCl₃) unless stated |
|---|---|---|
| H23 | 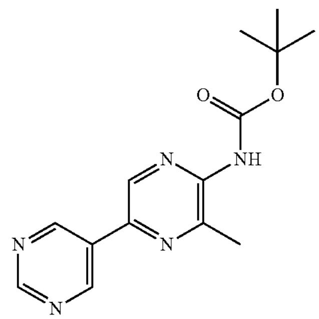 [SMILES: Cc1nc(-c2cncnc2)cnc1NC(=O)OC(C)(C)C] | 9.35 (s, 2H), 9.25 (s, 1H), 8.65 (s, 1H), 6.90 (br s, 1H), 2.65 (s, 3H), 1.55 (s, 9H) |
| H24 | 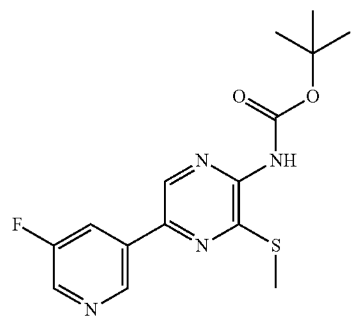 [SMILES: CSc1nc(-c2cncc(F)c2)cnc1NC(=O)OC(C)(C)C] | 9.05 (s, 1H), 8.60 (s, 1H), 8.55 (d, 1H), 8.00 (dd, 1H), 6.90 (br s, 1H), 2.70 (s, 3H), 1.55 (s, 9H) |
| H25 | 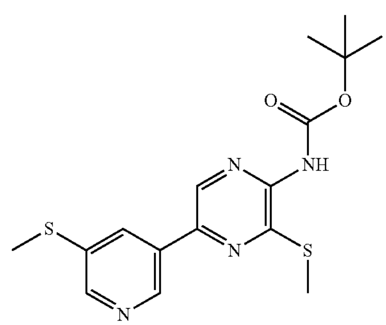 [SMILES: CSc1cncc(-c2cnc(NC(=O)OC(C)(C)C)c(SC)n2)c1] | 8.95 (s, 1H), 8.57-8.55 (m, 2H), 8.15 (t, 1H), 6.85 (br s, 1H), 2.75 (s, 3H), 2.60 (s, 3H), 1.60 (s, 9H) |
| H26 | 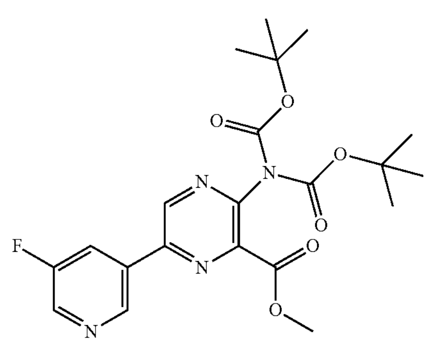 [SMILES: COC(=O)c1nc(-c2cncc(F)c2)cnc1N(C(=O)OC(C)(C)C)C(=O)OC(C)(C)C] | 9.12-9.10 (m, 2H), 8.65 (d, 1H), 8.20 (dd, 1H), 4.00 (s, 3H), 1.45 (s, 18H) |

TABLE 2-continued

Characterising data for compounds of Formula (I) made by the methods described above.

| Compound ID | Structure | Data (400 MHz, CDCl₃) unless stated |
|---|---|---|
| H27 | 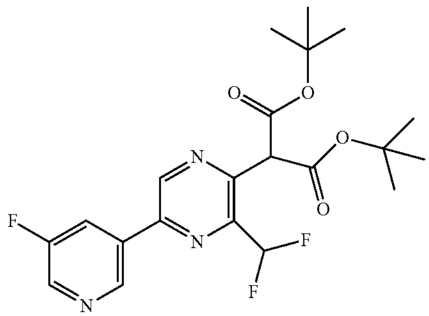 [SMILES: CC(C)(C)OC(=O)C(C(=O)OC(C)(C)C)c1ncc(-c2cncc(F)c2)nc1C(F)F] | 9.17-9.14 (m, 2H), 8.65 (d, 1H), 8.20 (dd, 1H), 6.78 (t, 1H), 1.45 (s, 18H) |
| H28 | 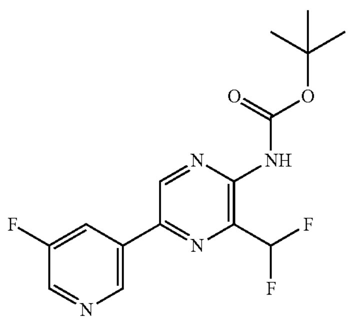 [SMILES: CC(C)(C)OC(=O)Nc1ncc(-c2cncc(F)c2)nc1C(F)F] | 9.05 (s, 1H), 9.00 (s, 1H), 8.60 (d, 1H), 8.05 (dd, 1H), 7.45 (br s, 1H), 6.88 (t, 1H), 1.55 (s, 9H) |
| H29 | 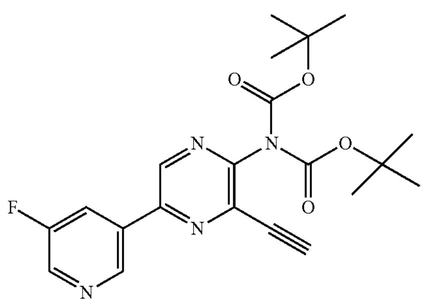 [SMILES: C#Cc1nc(-c2cncc(F)c2)cnc1N(C(=O)OC(C)(C)C)C(=O)OC(C)(C)C] | 9.10 (s, 1H), 8.90 (s, 1H), 8.60 (d, 1H), 8.15 (dd, 1H), 3.50. (s, 1H), 1.45 (s, 18H) |
| H30 | 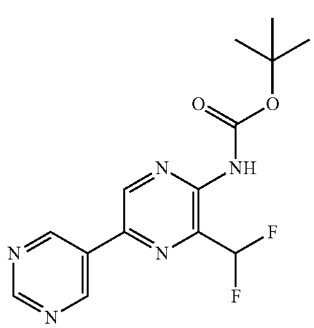 [SMILES: CC(C)(C)OC(=O)Nc1ncc(-c2cncnc2)nc1C(F)F] | 9.32-9.30 (m, 3H), 9.00 (s, 1H), 7.45 (brs, 1H), 6.90 (t, 1H), 1.60 (s, 9H) |

TABLE 2-continued

Characterising data for compounds of Formula (I) made by the methods described above.

| Compound ID | Structure | Data (400 MHz, CDCl$_3$) unless stated |
|---|---|---|
| H31 | (structure) | 9.45 (s, 2H), 9.40 (s, 1H), 9.10 (s, 1H), 6.80 (t, 1H), 1.45 (s, 18H) |
| H32 | (structure) | 9.10 (s, 1H), 8.80 (s, 1H), 8.60 (d, 1H), 8.20 (dd, 1H), 1.45 (s, 18H), 0.30 (s, 9H) |

Physical Characterisation

Compounds of the invention were characterised using one or more of the following methods.

NMR

NMR spectra contained herein were recorded on either a 400 MHz Bruker AVANCE III HD equipped with a Bruker SMART probe or a 500 MHz Bruker AVANCE III equipped with a Bruker Prodigy probe. Chemical shifts are expressed as ppm downfield from TMS, with an internal reference of either TMS or the residual solvent signals. The following multiplicities are used to describe the peaks: s=singlet, d=doublet, t=triplet, dd=double doublet, m=multiplet. Additionally br. is used to describe a broad signal and app. is used to describe an apparent multiplicity.

LCMS

LCMS data contained herein consists of the molecular ion [MH+] and the retention time (tr) of the peak recorded on the chromatogram. The following instruments, methods and conditions were used to obtain LCMS data:

Method A

Instrumentation: Waters Acquity UPLC-MS using a Sample Organizer with Sample Manager FTN, H-Class QSM, Column Manager, 2×Column Manager Aux, Photodiode Array (Wavelength range (nm): 210 to 400, ELSD and SQD 2 equipped with a Waters HSS T3 C18 column (column length 30 mm, internal diameter of column 2.1 mm, particle size 1.8 micron).

Ionisation method: Electrospray positive and negative: Capillary (kV) 3.00, Cone (V) 30.00, Source Temperature (° C.) 500, Cone Gas Flow (L/Hr.) 10, Desolvation Gas Flow (L/Hr.) 1000. Mass range (Da): positive 95 to 800, negative 115 to 800.

The analysis was conducted using a two minute run time, according to the following gradient table at 40° C.:

| Time (mins) | Solvent A (%) | Solvent B (%) | Flow (ml/mn) |
|---|---|---|---|
| 0.00 | 95.0 | 5.0 | 0.7 |
| 1.75 | 0.0 | 100 | 0.7 |
| 1.76 | 0.0 | 100 | 0.7 |
| 2.0 | 0.0 | 5.0 | 0.7 |
| 2.01 | 95.0 | 5.0 | 0.7 |
| 2.11 | 95.0 | 5.0 | 0.7 |

Solvent A: H$_2$O with 0.05% TFA
Solvent B: CH$_3$CN with 0.05% TFA

Method B (2 min Method)

Instrumentation: Either (a) Waters Acquity UPLC system with Waters SQD2 single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash); or (b) Waters Acquity UPLC system with Waters QDa single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash).

LC-Method

Phenomenex 'Kinetex C18 100A' column (50 mm×4.6 mm, particle size 2.6 micron), Flow rate: 2 mL/min at 313K (40 Celsius), Gradient (Solvent A: $H_2O$ with 0.1% Formic Acid; Solvent B: Acetonitrile with 0.1% Formic Acid):

The analysis was conducted using a two minute run time, according to the following gradient table at 40° C.

| Time (mins) | Solvent A (%) | Solvent B (%) | Flow (ml/mn) |
|---|---|---|---|
| Initial | 70.0 | 30.0 | 2.000 |
| 1.20 | 10.0 | 90.0 | 2.000 |
| 1.70 | 10.0 | 90.0 | 2.000 |
| 1.80 | 70.0 | 30.0 | 2.000 |
| 2.00 | 70.0 | 30.0 | 2.000 |
| 2.20 | 70.0 | 30.0 | 2.000 |

Method C (1 min Method)

Instrumentation: Either (a) Waters Acquity UPLC system with Waters SQD2 single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash); or (b) Waters Acquity UPLC system with Waters QDa single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash).

LC-Method

Phenomenex 'Kinetex C18 100A' column (50 mm×4.6 mm, particle size 2.6 micron), Flow rate: 2 mL/min at 313K (40 Celsius), Gradient (Solvent A: $H_2O$ with 0.1% Formic Acid; Solvent B: Acetonitrile with 0.1% Formic Acid):

The analysis was conducted using a one minute run time, according to the following gradient table at 40° C.

| Time (mins) | Solvent A (%) | Solvent B (%) | Flow (ml/mn) |
|---|---|---|---|
| Initial | 60.0 | 40.0 | 2.000 |
| 0.80 | 0.0 | 100.0 | 2.000 |
| 0.95 | 0.0 | 100.0 | 2.000 |
| 1.00 | 60.0 | 40.0 | 2.000 |
| 1.10 | 60.0 | 40.0 | 2.000 |
| 1.25 | 60.0 | 40.0 | 2.000 |

Biologicial Examples

B1 Pre-Emergence Herbicidal Activity

Seeds of a variety of test species were sown in standard soil in pots: *Triticum aestivium* (TRZAW), *Avena fatua* (AVEFA), *Alopecurus myosuroides* (ALOMY), *Echinochloa crus-galli* (ECHCG), *Lolium perenne* (LOLPE), and *Setaria faberi* (SETFA). After cultivation for one day (pre-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Table B1.

TABLE B1

Control of weed species by compounds of Formula (I) after pre-emergence application

| Compound ID | Rate (g/ha) | ECHCG | LOLPE | SETFA | AVEFA | ALOMY | TRAZW |
|---|---|---|---|---|---|---|---|
| H1 | 1000 | 4 | 1 | 4 | 2 | 0 | 0 |
| H2 | 1000 | 4 | 2 | 5 | 2 | 0 | 0 |
| H4 | 1000 | 4 | 1 | 5 | 3 | 0 | 0 |
| H5 | 1000 | 5 | 1 | 5 | 2 | 0 | 0 |
| H6 | 1000 | 3 | 0 | 4 | 1 | 0 | 1 |
| H7 | 1000 | 3 | 0 | 5 | 1 | 0 | 0 |
| H8 | 1000 | 1 | 1 | 2 | 0 | 0 | 0 |
| H9 | 1000 | 2 | 1 | 5 | 1 | 0 | 0 |
| H10 | 1000 | 2 | 0 | 4 | 0 | 0 | 0 |
| H11 | 1000 | 3 | 2 | 4 | 0 | 1 | 0 |
| H12 | 1000 | 1 | 0 | 4 | 0 | 0 | 0 |
| H13 | 1000 | 1 | 0 | 4 | 0 | 0 | 0 |
| H14 | 1000 | 2 | 2 | 3 | 0 | 0 | 0 |
| H15 | 1000 | 0 | 0 | 0 | 0 | 0 | 0 |
| H16 | 1000 | 1 | 0 | 1 | 0 | 0 | 0 |
| H17 | 1000 | 4 | 3 | 4 | 2 | 0 | 0 |
| H18 | 1000 | 3 | 1 | 4 | 0 | 0 | 0 |
| H19 | 1000 | 4 | 1 | 5 | 2 | 0 | 0 |
| H20 | 1000 | 2 | 1 | 4 | 2 | 0 | 1 |
| H21 | 1000 | 1 | 5 | 5 | 2 | 0 | 0 |
| H22 | 1000 | 0 | 0 | 0 | 0 | 0 | 0 |
| H23 | 1000 | 2 | 0 | 4 | 1 | 0 | 0 |
| H24 | 1000 | 2 | 1 | 5 | 2 | 0 | 0 |
| H25 | 250 | 0 | 0 | 0 | 0 | 0 | 0 |
| H26 | 1000 | 0 | 0 | 5 | 0 | 0 | 0 |
| H27 | 1000 | 4 | 0 | 4 | 2 | 0 | 0 |
| H28 | 1000 | 2 | 0 | 4 | 2 | 3 | 0 |
| H29 | 1000 | 0 | 0 | 0 | 0 | 0 | 0 |
| H30 | 1000 | 3 | 1 | 4 | 0 | 0 | 1 |
| H31 | 1000 | 2 | 0 | 2 | 1 | 2 | 0 |

Compounds that score 4 or 5 on one or more plant species are particularly preferred.

B2 Post-Emergence Herbicidal Activity

Seeds of a variety of test species were sown in standard soil in pots: *Triticum aestivium* (TRZAW), *Avena fatua* (AVEFA), *Alopecurus myosuroides* (ALOMY), *Echinochloa crus-galli* (ECHCG), *Lolium perenne* (LOLPE), and *Setaria faberi* (SETFA). After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Table B2.

TABLE B2

Control of weed species by compound of Formula (I) after post-emergence application

| Compound ID | Rate (g/ha) | ECHCG | LOLPE | SETFA | AVEFA | ALOMY | TRAZW |
|---|---|---|---|---|---|---|---|
| H1 | 1000 | 5 | 3 | 5 | 4 | 0 | 0 |
| H2 | 1000 | 5 | 2 | 5 | 3 | 0 | 0 |
| H4 | 1000 | 5 | 2 | 5 | 3 | 0 | 1 |
| H5 | 1000 | 5 | 2 | 5 | 3 | 0 | 1 |
| H6 | 1000 | 3 | 1 | 4 | 2 | 0 | 1 |
| H7 | 1000 | 5 | 2 | 5 | 3 | 0 | 1 |
| H8 | 1000 | 1 | 0 | 1 | 1 | 0 | 0 |
| H9 | 1000 | 3 | 1 | 5 | 3 | 0 | 0 |
| H10 | 1000 | 2 | 1 | 5 | 1 | 0 | 0 |
| H11 | 1000 | 3 | 2 | 5 | 2 | 0 | 0 |
| H12 | 1000 | 3 | 2 | 5 | 2 | 0 | 0 |
| H13 | 1000 | 2 | 1 | 5 | 1 | 0 | 1 |
| H14 | 1000 | 2 | 1 | 4 | 1 | 0 | 0 |
| H15 | 1000 | 0 | 0 | 2 | 1 | 0 | 0 |
| H16 | 1000 | 1 | 2 | 3 | 1 | 0 | 0 |
| H17 | 1000 | 4 | 3 | NT* | 3 | 2 | 0 |
| H18 | 1000 | 4 | 1 | 3 | 1 | 0 | 0 |
| H19 | 1000 | 4 | 2 | 5 | 3 | 0 | 0 |
| H20 | 1000 | 4 | 3 | 5 | 2 | 0 | 1 |
| H21 | 1000 | 4 | 4 | 5 | 4 | 1 | 1 |
| H22 | 1000 | 1 | 1 | 2 | 1 | 0 | 0 |
| H23 | 1000 | 4 | 2 | 5 | 3 | 1 | 1 |
| H24 | 1000 | 4 | 2 | 5 | 3 | 0 | 0 |
| H25 | 250 | 1 | 1 | 1 | 1 | 0 | 0 |
| H26 | 1000 | 3 | 0 | 5 | 1 | 0 | 1 |
| H27 | 1000 | 5 | 4 | 5 | 4 | 0 | 1 |
| H28 | 1000 | 5 | 3 | 5 | 4 | 0 | 0 |
| H29 | 1000 | 1 | 1 | 1 | 0 | 0 | 1 |
| H30 | 1000 | 4 | 2 | 4 | 3 | 1 | 1 |
| H31 | 1000 | 5 | 2 | 5 | 3 | 1 | 1 |

*NT = not tested

Compounds which score 4 or 5 on one or more plant species are particularly preferred.

The invention claimed is:
1. A compound of Formula (I)

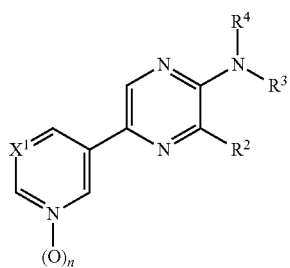

(I)

or a salt thereof, wherein, $X^1$ is N or $CR^1$;

$R^1$ is selected from the group consisting of hydrogen, halogen, cyano, $C_1$-$C_6$alkyl, $C_3$-$C_6$cycloalkyl, $C_2$-$C_6$alkenyl, $C_2$-$C_6$alkynyl, $C_1$-$C_6$alkoxy, —C(O)OC$_1$-$C_6$alkyl, —S(O)$_p$C$_1$-$C_6$alkyl, NR$^6$R$^7$, $C_1$-$C_6$haloalkoxy and $C_1$-$C_6$haloalkyl;

$R^2$ is selected from the group consisting of halogen, cyano, nitro, $C_1$-$C_6$alkyl, $C_1$-$C_6$haloalkyl, $C_2$-$C_6$alkenyl, $C_2$-$C_6$alkynyl, trimethylsilylC$_2$-$C_6$alkynyl-, $C_3$-$C_6$cycloalkyl, $C_5$-$C_6$cycloalkenyl, —C(O)OC$_1$-$C_6$alkyl, —S(O)$_p$(C$_1$-$C_6$alkyl), $C_1$-$C_6$alkoxy, $C_1$-$C_6$haloalkoxy, —(CR$^a$R$^b$)R$^{15}$, phenyl and benzyloxy;

$R^{15}$ is hydroxy, —C(O)OR$^c$, —OC(O)R$^{15}$, —C$_3$-$C_6$cycloalkyl, or an aryl, -aryloxy, -heteroaryl, -heteroaryloxy or -heterocyclyl ring, wherein said ring is optionally substituted by 1 to 3 independent R$^8$;

$R^3$ is —C(O)X$^2$R$^{12}$;

$X^2$ is O or NR$^{10}$;

$R^4$ is selected from the group consisting of hydrogen, $C_1$-$C_6$alkyl, $C_1$-$C_6$alkoxy, $C_1$-$C_6$haloalkyl, $C_1$-$C_6$haloalkoxy, $C_3$-$C_6$cycloalkyl, $C_3$-$C_6$alkenyl, $C_3$-$C_6$alkynyl, —C(O)R$^9$—(CR$^a$R$^b$)$_q$R$^5$, —C(O)X$^3$R$^{13}$; or, when $X^2$ is O, $R^{12}$ is selected from the group consisting of $C_1$-$C_6$alkyl, $C_r$alkoxyC$_s$alkyl, $C_1$-$C_6$haloalkyl, $C_r$alkoxyC$_s$haloalkyl, $C_r$alkylthioC$_s$alkyl, $C_2$-$C_6$alkenyl, $C_2$-$C_6$alkynyl, and —(CR$^a$R$^b$)$_q$R$^{11}$, or $R^4$ and $R^{12}$ together with the heteroatoms to which they are joined form a 5-7 membered ring system optionally containing 1 additional heteroatom selected from S, O and N, wherein when said additional heteroatom is sulphur it is in the form S(O)$_p$;

when $X^2$ is NR$^{10}$, $R^{12}$ is selected from the group consisting of hydrogen, $C_1$-$C_6$alkyl, $C_1$-$C_6$alkoxy, $C_1$-$C_6$haloalkyl, $C_1$-$C_6$haloalkoxy, $C_r$alkylthioC$_s$alkyl, $C_2$-$C_6$alkenyl, $C_2$-$C_6$alkynyl, and —(CR$^a$R$^b$)$_q$R$^{11}$; or $R^{10}$ and $R^{12}$ together with the nitrogen atom to which they are both joined, can form a 5-, 6-, or 7-membered ring, optionally containing 1 to 3 additional heteroatoms each independently selected from O, N or S, wherein when said ring contains a ring sulphur, said ring sulphur is in the form S(O)$_p$; or $R^4$ and $R^{10}$ together with the atoms to which they are joined form a 5-7 membered ring system optionally comprising from 1 or 2 additional heteroatoms independently selected from S, O and N and wherein when said ring system contains a ring sulphur, said ring sulphur is in the form S(O)$_p$, or, $R^{10}$ is independently selected from the group consisting of hydrogen, $C_1$-$C_6$alkyl, $C_3$-$C_6$ cycloalkyl;

when $R^4$ is —C(O)X$^3$R$^{13}$, $X^3$ is O or NR$^{14}$;

when $X^3$ is O, $R^{13}$ is selected from the group consisting of $C_1$-$C_6$alkyl, $C_r$alkoxyC$_s$alkyl, $C_1$-$C_6$haloalkyl, $C_r$alkoxyC$_s$haloalkyl, $C_r$alkylthioC$_s$alkyl, $C_2$-$C_6$alkenyl, $C_2$-$C_6$alkynyl, and —(CR$^a$R$^b$)$_q$R$^{11}$, or $R^3$ and $R^{13}$ together with the heteroatoms to which they are joined form a 5-7 membered ring system optionally containing 1 additional heteroatom selected from S, O and N, wherein when said additional heteroatom is sulphur it is in the form S(O)$_p$;

when $X^3$ is NR$^{14}$, $R^{13}$ is selected from the group consisting of hydrogen, $C_1$-$C_6$alkyl, $C_1$-$C_6$alkoxy, $C_1$-$C_6$haloalkyl, $C_1$-$C_6$haloalkoxy, $C_r$alkylthioC$_s$alkyl, $C_2$-$C_6$alkenyl, $C_2$-$C_6$alkynyl, and —(CR$^a$R$^b$)$_q$R$^{11}$; or $R^{14}$ and $R^{13}$ together with the nitrogen atom to which they are both joined, can form a 5-, 6-, or 7-membered ring, optionally containing 1 or 2 additional heteroatoms each independently selected from O, N or S, wherein when said ring contains a ring sulphur, said ring sulphur is in the form S(O)$_p$;

$R^a$ is hydrogen or $C_1$-$C_2$ alkyl;
$R^b$ is hydrogen or $C_1$-$C_2$ alkyl;
$R^c$ is hydrogen or $C_1$-$C_4$alkyl;
$R^5$ is cyano, —C(O)OC$_1$-$C_6$alkyl, —C$_3$-$C_6$cycloalkyl, -aryl or heteroaryl wherein said aryl and heteroaryl are optionally substituted by 1 to 3 independent R$^8$;
$R^6$ and $R^7$ are independently selected from the group consisting of hydrogen, $C_1$-$C_6$alkyl, and —C(O)OC$_1$-$C_4$alkyl;

each $R^8$ is independently selected from the group consisting of halogen, $C_1$-$C_6$alkyl and $C_1$-$C_6$alkoxy-, $C_1$-$C_6$ haloalkyl, $C_1$-$C_6$ haloalkoxy-, cyano and $S(O)_p(C_1$-$C_6$alkyl);

$R^9$ is selected from the group consisting of hydrogen, $C_1$-$C_6$alkyl, $C_1$-$C_6$alkoxy, $C_1$-$C_6$haloalkyl, $C_1$-$C_6$haloalkoxy, $C_2$-$C_6$alkenyl, $C_2$-$C_6$alkynyl, and —$(CR^aR^b)_qR^{11}$;

$R^{11}$ is cyano, —$C_3$-$C_6$cycloalkyl, or an -aryl, -heteroaryl or -heterocyclyl ring, wherein said ring is optionally substituted by 1 to 3 independent $R^8$, and wherein when said ring contains a ring sulphur, said ring sulphur is in the form $S(O)_p$;

n is 0 or 1;

p is 0, 1, or 2;

q is 0, 1, 2, 3, 4, 5 or 6;

r is 1, 2, 3, 4, or 5, s is 1, 2, 3, 4, or 5, and the sum of r+s is less than or equal to 6.

2. The compound of Formula (I) according to claim 1, wherein $X^1$ is N.

3. The compound of Formula (I) according to claim 1, wherein $X^1$ is $CR^1$ and $R^1$ is selected from the group consisting of cyano, halogen, $C_1$-$C_6$alkoxy, $C_1$-$C_6$haloalkoxy, $C_1$-$C_6$haloalkyl, and —$S(O)_pC_1$-$C_6$alkyl.

4. The compound of Formula (I) according to claim 1, wherein $R^2$ is selected from the group consisting of halogen, cyano, $C_1$-$C_4$alkyl, $C_3$-$C_6$cycloalkyl, $C_1$-$C_4$alkoxy, $C_1$-$C_4$haloalkyl, $C_1$-$C_4$thioalkyl, $C_2$-$C_4$alkenyl, $C_5$-$C_6$cycloalkenyl, $C_2$-$C_4$alkynyl, trimethylsilyl$C_2$-$C_4$alkynyl-, —$C(O)OC_1$-$C_4$alkyl, —$(CR^aR^b)_qR^{15}$, phenyl, and benzyloxy.

5. The compound of Formula (I) according to claim 1, wherein $X^2$ is O.

6. The compound of Formula (I) according to claim 5, wherein $R^{12}$ is selected from the group consisting of hydrogen, $C_1$-$C_6$alkyl, $C_r$alkoxyC_s$alkyl, $C_1$-$C_6$haloalkyl, $C_r$alkoxyC_s$haloalkyl, $C_r$alkylthioC_s$alkyl, $C_2$-$C_6$alkenyl, $C_2$-$C_6$alkynyl, and —$(CR^aR^b)_qR^{11}$.

7. The compound of formula (I) according to claim 1, wherein $X^2$ is $NR^{10}$.

8. The compound of formula (I) according to claim 7, wherein $R^{10}$ is hydrogen or $C_1$-$C_6$alkyl.

9. The compound of formula (I) according to claim 7, wherein $R^{10}$ is hydrogen or $C_1$-$C_6$alkyl, and $R^{12}$ is $C_1$-$C_4$alkyl, $C_1$-$C_3$alkoxy, —$(CH_2)_3SCH_3$, $C_1$-$C_3$haloalkyl, $C_3$-$C_6$alkynyl, or $(CR^aR^b)_qR^{11}$.

10. The compound of Formula (I) according to claim 1, wherein $R^4$ is selected from the group consisting of hydrogen, methyl, ethyl, allyl, but-2-yn-1-yl, $C(O)R^9$ where $R^9$ is $C_1$-$C_6$alkoxy, and —$(CH_2)_qR^5$ wherein q is 1 and $R^5$ is selected from the group consisting of c-propyl, —$CO_2$methyl, and phenyl optionally substituted by 1-2 groups $R^8$, wherein each $R^8$ is independently $C_1$-$C_3$alkyl or halogen.

11. The compound of Formula (I) according to claim 10, wherein $R^9$ is $C_1$-$C_6$alkoxy.

12. A herbicidal composition comprising a compound according to claim 1 and an agriculturally acceptable formulation adjuvant.

13. The herbicidal composition according to claim 12, further comprising at least one additional pesticide.

14. The herbicidal composition according to claim 13, wherein the additional pesticide is a herbicide or herbicide safener.

15. A method of controlling weeds at a locus comprising application to the locus of a weed controlling amount of a compound of formula (I) according to claim 1.

* * * * *